(12) United States Patent
Mühlbauer et al.

(10) Patent No.: US 11,351,327 B2
(45) Date of Patent: Jun. 7, 2022

(54) HME DEVICE FOR USE IN A BREATHING CIRCUIT OF A VENTILATION SYSTEM

(71) Applicant: Drägerwerk AG & Co. KGaA, Lübeck (DE)

(72) Inventors: Pierre Mühlbauer, Lübeck (DE); Stefan Kolk, Groß Grönau (DE); Manuel Altherr, Steinwenden (DE); Xenia Subenko, Neuenkirchen-Vörden (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 186 days.

(21) Appl. No.: 16/521,312

(22) Filed: Jul. 24, 2019

(65) Prior Publication Data
US 2019/0344039 A1 Nov. 14, 2019

Related U.S. Application Data

(62) Division of application No. 15/427,411, filed on Feb. 8, 2017, now abandoned.

(30) Foreign Application Priority Data

Feb. 9, 2016 (DE) .................... 10 2016 001 408.3

(51) Int. Cl.
*A61M 16/10* (2006.01)
*A61M 16/08* (2006.01)
*A61M 16/20* (2006.01)

(52) U.S. Cl.
CPC .... *A61M 16/1045* (2013.01); *A61M 16/0891* (2014.02); *A61M 16/201* (2014.02)

(58) Field of Classification Search
CPC .......... A61M 16/1045; A61M 16/0891; A61M 16/201; A61M 2210/1025; A61M 16/10; A61M 16/1075; A61M 16/14
See application file for complete search history.

(56) References Cited

U.S. PATENT DOCUMENTS 6,363,930 B1 * 4/2002 Clawson ........... A61M 16/1045
128/201.13
6,792,649 B2 9/2004 Paterson et al.
(Continued)

FOREIGN PATENT DOCUMENTS

CA 2725794 A1 12/2009
CN 102083491 A 6/2011
(Continued)

*Primary Examiner* — Nathan R Price
*Assistant Examiner* — Tasnim Mehjabin Ahmed
(74) *Attorney, Agent, or Firm* — McGlew and Tuttle, P.C.

(57) ABSTRACT

An HME device, used in a closed breathing circuit of a ventilation system, has a housing with an inlet opening and with an outlet opening, an HME chamber (50a; 50b; 50c; 50d; 50e; 50f; 50g; 50h; 50i) arranged between the inlet opening and the outlet opening for receiving an HME medium and a switching mechanism (70a; 70b; 70c; 70d; 70e; 70f; 70g; 70h; 70i). The HME device can be switched over between an HME mode (M1), in which an HME fluid passage is provided from the inlet opening through the HME chamber to the outlet opening, and a bypass mode (M2), in which a fluid bypass passage is provided from the inlet opening past the HME chamber through a bypass channel (80a; 80b; 80d; 80e; 80f; 80h) in the housing to the outlet opening. The bypass channel is blocked with respect to the HME chamber in the bypass mode (M2).

20 Claims, 16 Drawing Sheets

(56) References Cited

U.S. PATENT DOCUMENTS

| | | |
|---|---|---|
| 6,976,488 B2 | 12/2005 | Halperin |
| 7,069,928 B1 * | 7/2006 | Waldo, Jr. .......... A61M 16/1045 128/201.13 |
| 7,347,203 B2 | 3/2008 | Marler et al. |
| 7,594,509 B2 | 9/2009 | Burk |
| 2009/0301475 A1 | 12/2009 | Korneff |
| 2011/0226250 A1 | 9/2011 | Labollita et al. |

FOREIGN PATENT DOCUMENTS

| | | | |
|---|---|---|---|
| CN | 102781502 | A | 11/2012 |
| CN | 203885976 | U | 10/2014 |
| DE | 601 06 837 | T2 | 12/2005 |
| EP | 2 301 615 | A1 | 3/2011 |
| EP | 2319573 | A1 | 5/2011 |

* cited by examiner

HME DEVICE FOR USE IN A BREATHING CIRCUIT OF A VENTILATION SYSTEM

CROSS REFERENCE TO RELATED APPLICATIONS

This application is a divisional of, and claims the benefit of priority under 35 U.S.C. § 120 of, U.S. application Ser. No. 15/427,411 filed Feb. 8, 2017, which claims the benefit of priority under 35 U.S.C. § 119 of German Application 10 2016 001 408.3 filed Feb. 9, 2016, the entire contents of which are incorporated herein by reference.

FIELD OF THE INVENTION

The present invention pertains to an HME device (heat and moisture exchanger or humidification moisture exchanger) for use in a closed breathing circuit of a ventilation system. The HME device has a housing with an inlet opening and with an outlet opening as well as an HME chamber arranged between the inlet opening and the outlet opening for receiving an HME medium. Such an HME device can be switched over between an HME mode, in which the passage of a fluid from the inlet opening through the HME chamber to the outlet opening is provided, and a bypass mode, in which the passage of fluid is provided from the inlet opening past the HME chamber through a bypass channel to the outlet opening.

BACKGROUND OF THE INVENTION

Such HME devices are known in the state of the art. For example, U.S. Pat. No. 7,594,509 B2 shows an HME device, in which a first housing half with an inlet opening can be rotated relative to a second housing half with an outlet opening in order to switch over between an HME mode and a bypass mode. A similar principle of operation appears from DE 601 06 837 T2, U.S. Pat. No. 7,347,203 B2 as well as U.S. Pat. No. 6,976,488 B2. U.S. Pat. No. 6,976,488 B2 shows, furthermore, a solution in which an HME medium can be compressed by a plunger. However, liquid, which is located within the HME medium, can escape as a result and reach a respiratory system of a connected patient. In addition, the potentially contaminated plunger represents a risk of infection for a patient. In addition, it is problematic in all the above-mentioned HME devices that a contact may occur between a drug aerosol and the HME medium in the bypass mode in the phase of inhalation and in the phase of exhalation, as a result of which the flow resistance of the HME device may increase.

SUMMARY OF THE INVENTION

An object of the present invention is to take the above-described drawbacks at least partly into account in HME devices for use in a closed breathing circuit of a ventilation system. In particular, an object of the present invention is to provide a cost-effective HME device for use in a closed breathing circuit of a ventilation system, by means of which switching over is possible between an HME mode and a bypass mode in a simple and reliable manner and a contact between the drug aerosol and the HME medium can reliably be prevented at the same time.

According to a first aspect of the present invention, an HME device for use in a closed breathing circuit of a ventilation system is provided. The HME device has a housing with an inlet opening, with an outlet opening as well as with an HME chamber arranged between the inlet opening and the outlet opening for receiving an HME medium. The HME device has, further, a switching mechanism, by which the HME device can be switched over between an HME mode, in which the passage of an HME fluid is provided from the inlet opening through the HME chamber to the outlet opening, and a bypass mode, in which a fluid bypass passage is provided from the inlet opening past the HME chamber through a bypass channel in the housing to the outlet opening. The bypass channel is blocked according to the present invention against the HME chamber in the bypass mode.

The fact that the bypass channel of the HME device is blocked against the HME chamber in the bypass mode shall mean here that the bypass chamber is blocked or closed in an especially sealing manner against the HME chamber in the bypass mode, i.e., the bypass channel and the HME chamber are separated from one another in terms of fluid flow in the bypass mode, and no or essentially no fluid contact is therefore possible in the bypass mode between the bypass channel and the HME chamber and no fluidic interaction or essentially no fluidic interaction may occur between the bypass channel and the HME chamber. The HME chamber or an HME medium located in it is separated now on both sides from the bypass channel as well as from the inlet opening and the outlet opening. The HME chamber is preferably closed in the bypass mode, i.e., it is fluidically separated or essentially separated from the area surrounding the HME chamber. Due to the separation of the HME chamber from the bypass channel according to the present invention in the bypass mode, it is possible, for example, to prevent a drug aerosol from coming into contact with the HME medium during the atomization of a drug.

The HME chamber is not limited to a chamber with a single chamber space. It is possible, in particular, that the HME chamber has a chamber with a plurality of HME chamber sections. The HME chamber may, furthermore, be configured as a closed or opened chamber. The HME chamber can preferably be switched over between a closed state and an opened state. The HME chamber is especially preferably opened in the HME mode and, as was already shown above, closed, preferably completely, at least against the bypass channel in the bypass mode. The HME chamber is opened in the HME mode such that the passage of HME fluid from the inlet opening through the HME chamber to the outlet opening can be provided.

In the sense of the present invention, the inlet opening may also be an outlet opening and the outlet opening may also be an inlet opening. The concretization of the inlet opening and the outlet opening shall only be used in the embodiments for a simpler and clearer representation of the present invention.

An HME device is defined, in principle, as a heat and moisture exchanger known in the state of the art for ventilation systems. A fluid passage is defined according to the present invention especially as a possibility of fluid passage in a fluid channel, through which a fluid, for example, a drug aerosol or breathing air of a patient can flow. The switching mechanism is defined as a generic term for the elements of the HME device that are in a functional relationship and that are necessary for switching over between the HME mode and the bypass mode.

According to a variant of the present invention, the housing has an inlet-side housing half with the inlet opening and an outlet-side housing half with the outlet opening, the HME chamber being formed by an inner wall section of the inlet-side housing half and by an inner wall section of the outlet-side housing half, and the inlet-side housing half and the outlet-side housing half being arranged rotatably in relation to one another to block and open the bypass channel Due to the housing halves being mounted and arranged rotatably in relation to one another, the HME device can be switched over between the HME mode and the bypass mode in an especially simple manner. In addition, this makes possible a one-hand operation, in which, for example, only one of the two housing halves is rotated by a user against the other of the two housing halves. The two housing halves are preferably arranged rotatably relative to one another about the same axis of rotation. It may be advantageous in this connection if only one of the two housing halves is arranged rotatably in relation to the other of the two housing halves. However, both housing halves may also be arranged rotatably relative to one another about an axis of rotation. In the case in which only one of the two housing halves is arranged rotatably in relation to the other of the two housing halves, it may, further, be advantageous if the inlet opening corresponds to a passage opening in a fluid inlet channel and the outlet opening corresponds to a passage opening in a fluid outlet channel, wherein a rotatable housing half is arranged rotatably relative to the fluid inlet channel of the other housing half as well as to the fluid outlet channel. It can be achieved as a result that when rotating one housing half or when switching over between the HME mode and the bypass mode, neither the fluid inlet channel nor the fluid outlet channel is rotated. As a result, connection tubes or corresponding channels can be fastened to the fluid inlet channel and/or the fluid outlet channel especially tightly or in an especially fluid-tight manner. The HME device preferably has a turning handle, which is arranged on at least one of the two housing halves in order to rotate the housing halves more easily in relation to one another. Due to the rotation of the housing halves, the corresponding inner wall sections of the housing halves are rotated, as a result of which the HME chamber is correspondingly opened or closed or blocked. The inlet-side housing half may, of course, also be an outlet-side housing half in the sense of the present invention and the outlet-side housing half may, of course, also be an inlet-side housing half in the sense of the present invention. All inlet elements according to the present invention may also be defined as being outlet elements and all outlet elements according to the present invention may also be defined as inlet elements.

Further, it is possible according to the present invention that the inlet-side housing half has first inlet holes, second inlet holes, inlet diaphragms and inlet diaphragm passages between the inlet diaphragms and the outlet-side housing half has outlet holes and outlet diaphragms, wherein the first inlet holes and the inlet diaphragm passages are covered by the outlet diaphragms in the bypass mode and the second inlet holes are arranged at least partly flush with the outlet holes. Due to the coverage of the first inlet holes and of the inlet diaphragm passages by the outlet diaphragms or through same, it is possible to reliably prevent a contact between the drug aerosol and the HME medium in the bypass mode and to block the bypass channel against the HME chamber. Due to the two inlet holes being arranged at least partly flush with the outlet holes, a fluid bypass passage from the inlet opening past the HME chamber to the outlet opening can be guaranteed. The first inlet holes are preferably arranged uniformly around an axis of rotation. The second inlet holes are preferably also arranged uniformly around an axis of rotation. The first inlet holes and the second inlet holes are especially arranged around the same axis of rotation and are located at spaced locations from one another in the longitudinal direction of the axis of rotation, being especially located at spaced locations from one another over the full circumference in the longitudinal direction of the axis of rotation. The first and second passage holes are, in addition, arranged and configured offset in relation to one another preferably in the circumferential direction of the axis of rotation, i.e., the first and second passage holes are not preferably arranged flush or essentially flush with one another along a straight line or plane that is parallel or essentially parallel to the axis of rotation. However, the first inlet holes are arranged flush with the inlet diaphragm passages in at least some sections along the straight line or plane that is parallel or essentially parallel to the axis of rotation. The circumstance that the inlet holes and the inlet diaphragm passages are covered by the outlet diaphragms means in the sense of the present invention that the outlet diaphragms cover, seal and/or close the inlet holes and the inlet diaphragm passages in a fluid-tight manner According to this variant, a fluid bypass passage is provided in the bypass mode from the inlet opening past the HME chamber through the bypass channel and through the second inlet holes and the outlet holes to the outlet opening. A fluid bypass passage is correspondingly also provided from the outlet opening past the HME chamber through the bypass channel and through the outlet holes and the second inlet holes to the inlet opening. In the HME mode, i.e., after rotation of the first housing half in relation to the second housing half, the second inlet holes are opened by wall sections between the outlet holes and the outlet holes are covered by wall sections between the second inlet holes and the first inlet holes as well as the inlet diaphragm passages, i.e., they are no longer covered by the outlet diaphragms. As a result, an HME fluid passage is provided from the inlet opening through the first inlet holes, the HME chamber, the inlet diaphragm passages to the outlet opening. At the same time, an HME fluid passage is correspondingly provided from the outlet opening through the inlet diaphragm passages, the HME chamber and the first inlet holes to the inlet opening.

In addition, it is possible according to the present invention that a bistable holding mechanism, by which the two housing halves can be held in defined or predefined, different positions or end positions in relation to one another, is formed on the inlet-side housing half and/or on the outlet-side housing half Intermediate switching positions between the HME mode and the bypass mode can reliably be prevented thereby. A bistable holding mechanism is defined here as a holding mechanism that can assume two possible states and can change over into the other state by an external force or input only. The bistable holding mechanism has, for example, a convex projection on an outer wall section of a housing half, via which a grip element of the other housing half can be displaced in at least some sections, especially in the area of the greatest arch of the convex projection, based on a surface friction between the convex projection and the grip element. When the grip element is moved over the outer contour of the convex projection, a restoring force is generated, which acts up to the point of the greatest deflection. If the grip element is moved beyond this point over the described contour, a force acts in the direction of a switchover motion between the HME mode and the bypass mode. Only one of the two modes, i.e., the HME mode or the bypass mode, can thus be active, without intermediate switching states being able to be reached. A stop each is provided for the grip element in the respective position or end position in order to hold and/or lock the grip element securely in the particular end position. The bistable holding mechanism may correspondingly also be configured as a bistable locking mechanism.

According to another aspect of the present invention, the HME chamber is configured by an inner wall section of the housing and an outer wall mechanism of a displacing device of the HME device for displacing the HME medium, the displacing device being arranged movably for blocking the bypass channel in the bypass mode in relation to the HME chamber. An HME device of an especially simple design, in which a contact between drug aerosol and HME medium can nevertheless reliably be prevented in the bypass mode, can be provided due to the movably arranged partition. The displacing device is preferably configured in the form of a partition and it displaces the HME medium by compressing said medium and correspondingly allows it to recover again, i.e., a displacement of the HME medium is defined here as a displacement of the HME medium or of a part of the HME medium in at least some sections.

In addition, it is possible according to the present invention that the outer wall section is configured as a wall section that is elastically deformable at least partly or in at least some sections for displacing the HME medium and/or for blocking the bypass channel in the bypass mode in relation to the HME chamber. The outer wall section is defined here especially as a wall section with an outer wall surface. In such an embodiment variant, the outer wall section can be moved and/or deformed by a separate actuating device or directly. The outer wall section or the displacing device is preferably configured such that it is elastically deformable at least in the area in which it can come into direct contact with an HME medium in the HME chamber. The displacing device may have here, for example, a plate-shaped partition section, which is arranged in a bent state in the housing. More precisely, the plate-shaped partition section may be in contact with an inner wall section or an inner wall surface of the housing in an HME mode in an HME position. The plate-shaped partition section may be arranged and configured here such that in case of a switchover from the HME mode into the bypass mode, it can be moved from the HME position into a bypass position, for which the plate-shaped partition section is moved and/or deformed from the one inner wall section in the direction of an opposite inner wall section and out of the HME fluid passage.

In addition, it may be advantageous according to the present invention if the displacing device has two plate-shaped partition sections for separating the HME medium in at least some sections, wherein at least one of the two plate-shaped partition sections are arranged movably for displacing the HME medium and/or for blocking the bypass channel in the bypass mode against the HME chamber. Compared to one embodiment variant, in which the displacing device has only a single plate-shaped partition section, only a relatively slight motion and/or deformation of the partition section is necessary in case of the movably arranged partition section to switch over between the HME mode and the bypass mode. Further, it is advantageous here that the HME medium must be displaced and/or deformed only correspondingly slightly.

In addition, it may be advantageous within the framework of the present invention if at least one of the two plate-shaped partition sections for displacing the HME medium and/or for blocking the bypass channel in the bypass mode against the HME chamber is configured as an at least partly elastically deformable partition section. The elastically deformable partition section is preferably configured as an elastically deformable partition section at least in the area in which it can or does come into direct contact with an HME medium in the HME chamber. A switchover between the HME mode and the bypass mode is possible in an especially simple manner especially due to the combination of a stationary plate-shaped partition section and an at least partly elastically deformably configured partition section, because only the at least partly elastically deformable partition section must be deformed for the switchover.

It is possible according to a variant of the present invention that at least one of the two plate-shaped partition sections for displacing the HME medium and/or for blocking the bypass channel in the bypass mode against the HME chamber is arranged movably relative to the other plate-shaped partition section. Switchover is likewise possible in an especially simple manner between the HME mode and the bypass mode due to the combination of a stationary plate-shaped partition section and a movably arranged and/or configured partition section, because only the movably arranged partition section must be moved for the switchover.

In addition, it may be advantageous within the framework of the present invention if the two plate-shaped partition sections are arranged in the HME mode such that they are bent in the same first direction and at least one of the two plate-shaped partition sections for displacing the HME medium and/or for blocking the bypass channel in the bypass mode against the HME chamber is configured as a partition section deformable elastically in a second direction, which is opposite the first direction. It can be ensured hereby that the freest possible and most obstacle-free HME fluid passage possible is established through the HME medium in the HME mode. In addition, it is possible as a result to form a bypass channel for the bypass mode in an especially simple manner, namely by deforming the at least one plate-shaped partition section in the second direction.

In addition, it is possible according to the present invention that the displacing device or at least one of the two plate-shaped partition sections is arranged and configured elastically deformably such that the displacing device or the at least one of the two plate-shaped partition sections is deformable in a bistable manner, especially due to a residual stress of the displacing device of the at least one of the two plate-shaped partition sections, into a second HME end position or into a bypass end position. As a result, intermediate switching states between the HME mode and the bypass mode can reliably be prevented. The displacing device or the at least one of the two plate-shaped partition sections are arranged here in the housing preferably under a prestress. In addition, it is conceivable within the framework of the present invention that the displacing device or at least one of the two plate-shaped partition sections has a shape memory alloy, which is deformable such that the displacing device or at least one of the two plate-shaped partition sections is correspondingly deformable into the respective end position.

Another advantage may be that the displacing device is fixed in the housing at at least one point. A defined deflection and/or deformation of the displacing device can be facilitated hereby. It is especially preferred in this connection if the displacing device is fixed in the housing at two or four points. The displacing device is mounted here in the housing movably or pivotably in at least some sections about an axis of rotation or about two axes of rotation, i.e., the displacing device is fixed in the housing in the area of the axes of rotation or on corresponding shafts such that only a rotary motion but no translatory motion of the displacing device or of a section of the displacing device is possible. The displacing device can be moved and/or deformed hereby via a lever in an especially simple manner. This facilitates the desired one-hand actuation of the HME device according to the present invention.

In addition, it is possible according to the present invention that at least one manual actuating device is arranged for moving or elastically deforming the displacing device. The manual actuating device is defined in the sense of the present invention as an adjusting element, via which a user can move or elastically deform the displacing device by direct manual actuation.

It is, further, advantageous according to the present invention if the manual actuating device is connected to the displacing device, especially to one of the two plate-shaped partition sections and is especially configured monolithically with the displacing device. A reliable and precise displacement and/or deformation of the HME medium can be achieved due to the permanent connection between the displacing device and the manual actuating device. A monolithic or one-piece configuration of the displacing device with the manual actuating device simplifies the manufacturing process for manufacturing the HME device and leads to correspondingly low manufacturing costs.

In addition, it may be advantageous within the framework of the present invention if the manual actuating device has a lifting and rotating mechanism actuatable by pressing for moving and/or elastically deforming the displacing device, especially at least one of the two plate-shaped partition sections. The lifting and rotating mechanism is preferably configured as a bistable switching mechanism, i.e., the lifting and rotating mechanism according to the present invention can move and/or displace the displacing device or the at least one of the two plate-shaped partition sections into two possible end positions. More precisely, the lifting and rotating mechanism is configured such that the displacing device or the at least one of the two plate-shaped partition sections is moved into a first end position by a first pressure actuation of the lifting and rotating mechanism and the displacing device or the at least one of the two plate-shaped partition sections is moved into a second end position from the first end position by a second pressure actuation of the lifting and rotating mechanism. The lifting and rotating mechanism is preferably configured here in the form of a "retractable ballpoint pen mechanism" and shall not therefore be explained here in more detail. Intermediate switching states between the HME mode and the bypass mode can reliably be prevented by providing such a lifting and rotating mechanism.

In a variant of the present invention, the two partition sections have an outer wall surface and an inner wall surface each, wherein the outer wall surfaces correspond to the outer wall section and the inner wall surfaces correspond to an inner wall section of the bypass channel, i.e., the partition sections may form both a part of the HME chamber and a part of the bypass channel. An especially material-saving and hence also correspondingly cost-effective HME device can be provided hereby. The inner wall surfaces of the partition sections are located directly on one another and at one another in the HME mode. It is only for the bypass mode that the inner wall surfaces of the partition sections are arranged at spaced locations from one another such that they can form a part of the bypass channel. The circumstance that the outer wall surfaces correspond to the outer wall section and the inner wall surfaces correspond to the inner wall section means that the outer wall surfaces correspond to the outer wall section in at least some sections and the inner wall surfaces correspond to the inner wall section in at least some sections or are configured as same.

According to another aspect of the present invention, the displacing device has a stationary separating device and a movable separating device, wherein the movable separating device is arranged pivotably about an axis of rotation relative to the stationary separating device. As a result, the switchover between the HME mode and the bypass mode can be embodied in an especially simple manner. The movable separating device is preferably arranged fully pivotably. The movable separating device may be mounted pivotably in the housing at an inner wall section of the housing or at a frame element in the housing. The stationary separating device may likewise be fastened to an inner wall section of the housing or to a frame element in the housing. The frame element may be configured, for example, as an HME storage frame, which is provided in the housing for receiving the HME medium and is preferably fixed or fastened in the housing. The HME storage frame may have, further, an outer circumferential wall section, which is fastened in at least some sections on an inner wall section of the housing. To increase the rigidity, the HME storage frame may have struts. In a preferred embodiment variant, the movable separating device and/or the stationary separating device are fixed each at one of the struts and mounted pivotably. The HME medium can be displaced or compressed and moved in the process out of or into the fluid bypass passage by pivoting the movable separating device.

According to a variant of the present invention, the stationary separating device and the movable separating device may have each an outer wall surface and an inner wall surface. wherein the outer wall surfaces correspond to the outer wall section and the inner wall surfaces correspond to an inner wall section of the bypass channel. As a result, an especially material-saving and hence also correspondingly cost-effective HME device is provided. The inner wall surfaces of the separating device lie on one another in at least some sections in the HME mode, and the inner wall surfaces are located at spaced locations from one another to form a bypass channel in the HME mode.

In addition, it is possible according to the present invention that at least one manual actuating device is arranged outside the housing displaceably in the circumferential direction of the housing for pivoting the movable separating device. As a result, the movable separating device can be adjusted into the desired position in a simple manner and it can thus be switched over between the HME mode and the bypass mode in a correspondingly simple manner.

It is advantageous here if the manual actuating device is permanently connected to the movable partition and is configured especially monolithically with the movable separating device. Due to the permanent connection between the movable separating device and the manual actuating device, reliable and accurate motion of the movable separating device and hence a correspondingly reliable and accurate switchover between the HME mode and the bypass mode can be guaranteed. If the movable separating device and the manual actuating device are configured as a monolithic component, this simplifies the manufacturing process for the HME device and the cost can correspondingly be reduced.

According to another aspect of the present invention, the HME chamber is configured by an inner wall section of the inlet-side housing half, by an inner wall section of the outlet-side housing half and by an outer wall section of a displacing device of the HME device for displacing the HME medium, the displacing device having a first separating device and a second separating device for blocking the bypass channel in the bypass mode against the HME chamber, the first separating device and the second separating device being arranged pivotably about an axis of rotation in relation to one another, and the first separating device being in functional connection with one of the inlet-side housing half and of the outlet-side housing half and the second separating device being in functional connection with the other of the inlet-side housing half and of the outlet-side housing half. It is possible as a result to achieve a simple switchover between the HME mode and the bypass mode by rotating the housing halves. The housing halves do not have to be rotated completely against one another. It is decisive that the HME medium is sufficiently compressed by the first separating device and the second separating device, i.e., it is pressed apart such that it is arranged outside the fluid bypass passage from the inlet opening to the outlet opening. For example, a rotation of the housing halves in relation to one another by less than 60°, preferably by a value between 30° and 45°, is sufficient here.

It is possible according to a variant of the present invention that the first separating device and the second separating device have an outer wall surface and an inner wall surface each, wherein the outer wall surfaces correspond to the outer wall section and the inner wall surfaces correspond to an inner wall section of the bypass channel. An especially material-saving and correspondingly cost-effective HME device is created hereby. The inner wall surfaces lie on one another in the HME mode. The inner wall surfaces are arranged at spaced locations from one another in the bypass mode to form the bypass channel and are arranged at correspondingly spaced locations from one another to form the bypass channel.

In addition, it is possible according to the present invention that the first separating device is fastened to one of the inlet-side housing half and of the outlet-side housing half and is configured especially monolithically with the corresponding housing half, and the second separating device is fastened to the other of the inlet-side housing half and of the outlet-side housing half, and is configured especially monolithically with the corresponding housing half Due to the separating device being fastened according to the present invention to the housing halves, an especially reliable and defined displacement or shifting of the HME medium in the housing and in the HME chamber can be guaranteed. If the separating device and the housing halves are each configured as a monolithic component, this simplifies the manufacturing process for the HME device and the costs can correspondingly be reduced.

It is possible according to another aspect of the present invention that a hollow section is arranged in the housing rotatably about an axis of rotation and an inner wall section of the HME chamber corresponds to an inner wall section of the hollow section and a section of the bypass channel can be established between a first outer wall section of the hollow section and a first inner wall section of the housing, and the first outer wall section of the hollow section especially corresponds to an inner wall section of the bypass channel. The circumstance that the inner wall section of the HME chamber corresponds to the inner wall section of the hollow section means that the inner wall section of the HME chamber corresponds to the inner wall section of the hollow section and is configured as same. The circumstance that the first outer wall section of the hollow section corresponds to the inner wall section of the bypass channel means that the first outer wall section of the hollow section corresponds to the inner wall section of the bypass channel and is configured as same. The HME medium does not have to be displaced or deformed in the hollow section according to the present invention in order to be moved out of the HME fluid channel. It is thus possible to switch over between the HME mode and the bypass mode with a correspondingly low resistance and with the expenditure of a correspondingly weak force. Due to the fact that a section of the bypass channel can be established between the first outer wall section of the hollow section and the first inner wall section of the housing and that, in particular, the first outer wall section of the hollow section corresponds to the inner wall section of the bypass channel, an especially material-saving and hence correspondingly cost-effective HME device can, in addition, be provided.

It is possible according to a variant of the present invention that a second outer wall section of the hollow section is flush-integrated or essentially flush-integrated in contact with a second inner wall section of the housing. As a result, the HME device can be provided as an especially space-saving device. The second outer wall section is preferably arranged now flush-integrated at the second inner wall section such that the second outer wall section and the second inner wall section can be moved or rotated in relation to one another without great friction. It may be advantageous for this that the second outer wall section as well as the second inner wall section are configured in at least some sections as slide bearings, with slide bearing properties or with a surface roughness for slide bearing properties.

Moreover, it is possible within the framework of the present invention that the HME chamber is formed by an inner wall section of the hollow section and by an inner wall section of the housing. The HME device can thus be provided in an especially space-saving and hence correspondingly cost-effective manner as well.

It is also advantageous in this connection if the housing has a housing window, through which the hollow section is exposed section by section to the outside. It is easy as a result for a user of the HME device to rotate the hollow section, which is arranged essentially in the housing by a manual actuation of the hollow section for switching over between the HME mode and the bypass mode. It is especially advantageous in this case if an outer wall section or an outer wall surface of the hollow section, which can be rotated, visibly from the outside, into the housing window, has an HME marking for the bypass mode, for example, "bypass" or "aerosol." The markings may be arranged on the outer wall section of the hollow section such that the HME marking can be seen on the housing window in the HME mode and the bypass marking can be seen on the housing window in the bypass mode. A user can thus recognize immediately whether the HME device is currently in the HME mode or in the bypass mode.

According to another aspect of the present invention, the housing has a fluid inlet channel and a fluid outlet channel, the fluid inlet channel being connected to a first fluid switchover channel and the outlet channel being connected to a second fluid switchover channel, the first fluid switchover channel extending at right angles to the fluid inlet channel and the second fluid switchover channel extending at right angles to the fluid outlet channel, and the fluid inlet channel, the first fluid switchover channel, the second fluid switchover channel and the fluid outlet channel corresponding, in at least some sections, to the bypass channel in the bypass mode. This represents a further alternative embodiment variant, by means of which switchover is possible between the HME mode and the bypass mode in a simple and reliable manner and a contact between drug aerosol and HME medium can at the same time reliably be prevented. The fluid inlet channel and the fluid outlet channel are preferably configured connected components. The first fluid switchover channel preferably extends at right angles to the fluid inlet channel such that an angle between 100° and 170°, especially preferably between 120° and 150° is formed between the first fluid switchover channel and the fluid inlet channel. The second fluid switchover channel preferably extends at right angles to the fluid outlet channel such that an angle between 100° and 170°, especially preferably 120° and 150° is formed between the second fluid switchover channel and the fluid outlet channel. The space available in the housing can be utilized especially advantageously as a result. The first fluid switchover channel and the second fluid switchover channel are preferably configured here such that there is a flush connection between the first fluid switchover channel and the second fluid switchover channel in the bypass mode, especially between a ring-shaped end face of the first fluid channel and a ring-shaped end face of the second fluid channel, in at least some sections, i.e., the first fluid switchover channel and the second fluid switchover channel and the respective end faces thereof abut against each other in a flush-integrated manner, especially in a fluid-tight flush-integrated manner.

According to a variant of the present invention, the first fluid switchover channel and the second fluid switchover channel are arranged, in at least some sections, in parallel or essentially in parallel to one another in the HME mode. Due to such an arrangement and configuration of the fluid switchover channels, the space available in the housing or in the HME chamber can be utilized especially advantageously. In addition, an especially uniform design of the HME device can be obtained hereby, as a result of which identical or at least very similar components can be used, which in turn leads to a simple and cost-effective manufacture of the HME device.

Moreover, it is conceivable according to the present invention that the HME medium is arranged in the HME chamber and the HME medium has a stepped passage channel, in which one of the fluid inlet channel and the fluid outlet channel is arranged displaceably and the other of the fluid inlet channel and of the fluid outlet channel is arranged, in at least some sections, circumferentially in a positive-locking or flush-integrated manner with the HME medium. It can be ensured hereby that the HME medium is held in a defined position when the fluid channel, which is arranged displaceably in the HME medium, is displaced or moved. To arrange the fluid inlet channel or the fluid outlet channel displaceably or movably in the HME medium, the HME medium has a C-shaped, essentially C-shaped recess or a recess bent or extending in the circumferential direction of the HME medium, in which the fluid inlet channel or the fluid outlet channel can move, without displacing or deforming the HME medium. The stepped passage channel is defined in the sense of the present invention as a passage opening in the HME medium, which is not configured as a continuous passage opening but is configured with a step or with an edge, i.e., with a step between an inlet opening and an outlet opening of this passage opening.

According to another aspect of the present invention, the housing has an inlet-side housing half and an outlet-side housing half, wherein an fluid inlet channel is arranged in the inlet-side housing half. The fluid inlet channel and the inlet-side housing half are arranged rotatably relative to one another, and the fluid inlet channel has an inlet opening, which corresponds to the inlet opening of the HME device, and a passage opening. The passage opening is directed into the HME chamber in the HME mode and into the bypass channel in the bypass mode. A further embodiment variant is provided hereby, by means of which an especially simple switchover is possible between the HME mode and the bypass mode. It is, in addition, possible due to the configuration according to the present invention to embody an especially material-saving and hence correspondingly cost-effective HME device. In particular, the inlet-side housing half is arranged according to the present invention rotatably in relation to the fluid inlet channel as well as to the outlet-side housing half. As a result, a user of this HME device is able to switch over between the HME mode and the bypass mode by rotating the inlet-side housing half in an especially simple manner Due to the fact that only the inlet-side housing half is rotated during a switchover between the HME mode and the bypass mode, while the fluid inlet channel as well as the outlet-side housing half are not moved, fluid channels can be arranged in an especially rigid and fluid-tight manner at the fluid inlet channel and the outlet-side housing half. The fluid inlet channel protrudes according to the present invention into the inlet-side housing half in at least some sections and through the inlet-side housing half until it comes into contact with the outlet-side housing half, with which the fluid inlet channel is preferably in contact in at least some sections in a flush-integrated manner Due to this coupling of the fluid inlet channel with the inlet-side housing half as well as with the outlet-side housing half in case of the above-described rotatable mounting at least of the inlet-side housing half, an HME device, which has an especially simple design and yet functions reliably, can be created. The passage opening described in connection with this embodiment is defined especially as an outlet-side opening in the fluid inlet channel. This opening is not limited here to a circular pipe opening. This passage opening may rather also have different opening sections or an opening area having any desired geometric shape.

According to a variant of the present invention, it is advantageous if the passage opening has a lateral opening section and a frontal opening section, the opening direction of the lateral opening section being directed at right angles to the opening direction of the inlet opening and/or of the frontal opening section. The lateral opening section and the frontal opening section may be separated here from one another by a web or another separating area or provided as sections of a single opening or passage opening. It is possible as a result that an HME fluid passage is provided from the inlet opening through the lateral opening section into the HME medium and from the HME medium through the frontal opening section farther through the outlet opening. If the inlet-side housing half is rotated now relative to the fluid inlet channel, i.e., if there is a switchover from the HME mode into the bypass mode, a fluid bypass passage is provided from the inlet opening through the lateral opening section into a bypass chamber and from the bypass chamber through the frontal opening section farther through the outlet opening. The bypass channel corresponds in this case to a channel section that is formed by the fluid inlet channel, the inlet-side housing half and the outlet-side housing half. It is especially advantageous in this connection if an HME chamber, which occupies at least 50%, preferably more than 70% of the volume or of an inner volume area of the inlet-side housing half, which area is defined by an inner wall section of the inlet-side housing half and an open area thereof, is formed in the inert-side housing half.

Further, it is possible according to the present invention that the fluid inlet channel has a wall section that is arranged, especially flush with the lateral opening section, in the fluid inlet channel in parallel to or essentially in parallel to the opening direction of the lateral opening section. As a result, a fluid passage or a corresponding fluid can advantageously be sent in the direction of the HME chamber or the bypass chamber through the lateral opening section. The wall section is preferably a monolithic component of the fluid inlet channel, but it may also be arranged as a separate component. The wall section is preferably configured at right angles, especially preferably mutually perpendicularly or essentially mutually perpendicularly to an inner wall section or an inner wall surface of the fluid inlet channel. As a result, an especially efficient bypass can be achieved from the fluid inlet channel in the direction of the HME chamber or from the bypass chamber.

Moreover, it is possible in the sense of the present invention that the wall section has a height that corresponds to at least half of the height, especially to the entire passage height of the fluid inlet channel at the site of the wall section. As a result, the fluid passage or a corresponding fluid can be sent especially effectively in the direction of the HME chamber or the bypass chamber. To reduce turbulent flows or to reduce flow resistances, the wall section may have, in at least some sections, a convex and/or concave wall surface, which sends a fluid flow from the inlet opening better in the direction of the HME chamber or the bypass chamber and prevents the fluid flow from impinging against the wall section with full force at right angles or in a mutually perpendicular direction.

According to another aspect of the present invention, an HME storage frame is arranged in the housing for storing the HME medium and the HME storage frame is mounted rotatably about an axis of rotation for switching over between the HME mode and the bypass mode, the HME storage frame having an outer ring section and a storage frame passage channel within the outer ring section, the HME chamber being formed by an inner wall section of the housing, by an inner wall section of the outer ring section and by an outer wall section of the storage frame passage channel, and an inner wall section of the storage frame passage channel corresponding to an inner wall section in the bypass mode. An additional embodiment variant is provided by this, by means of which an especially simple switchover is possible between the HME mode and the bypass mode. The storage frame passage channel is preferably configured as an inner ring section, i.e., is correspondingly ring-shaped, especially in the form of a closed ring. The outer ring section and the inner ring section or the storage frame passage channel are preferably connected to one another by connection struts, which are surrounded or can be enclosed by the HME medium. As a result, the storage frame passage channel can be held in a stable manner in the outer ring section. Both parts of the HME chamber and parts of the bypass channel are configured by the present HME storage frame. As a result, an especially material-saving and correspondingly cost-effective solution is obtained for providing the HME device according to the present invention. The storage frame passage channel is preferably arranged eccentrically in the outer ring section and/or in the hosing. As a result, the storage frame passage channel can be rotated out of the HME fluid passage or the fluid bypass passage in a simple manner by rotating the HME storage frame.

It is advantageous in a variant of the present invention if an outer wall section of the outer ring section is in contact with an inner wall section of the housing in a flush-integrated manner. As a result, the HME storage frame can be twisted or rotated in the housing about the axis of rotation especially reliably and at the same time with low resistance and it can make possible a correspondingly simple switchover between the HME mode and the bypass mode.

Further, it is possible according to the present invention that an outer wall section of the outer ring section is functionally connected through a housing window to an adjusting element arranged outside the housing, and the HME storage frame is rotatable about the axis of rotation by moving the adjusting element. As a result, the HME storage frame can be rotated about the axis of rotation in an especially simple manner and switched over in a correspondingly simple manner between the HME mode and the bypass mode. The housing window is preferably sealed or closed in a fluid-tight manner against the HME chamber.

In addition, it may be advantageous in the sense of the present invention if the adjusting element surrounds the housing in a ring-shaped manner in at least some sections. It is possible as a result that a user can easily grasp the adjusting element for switching over between the HME mode and the bypass mode in each position and can rotate the HME storage frame in a correspondingly simple and user-friendly manner. The outer wall section of the ring-shaped section of the adjusting element is preferably profiled, i.e., it is provided with recessed grips and/or projections. As a result, the adjusting element can also be grasped properly with, for example, wet hands, and the HME storage frame can rotate correspondingly well. The adjusting element is always connected here functionally to the HME storage frame.

Moreover, it is possible according to the present invention that the adjusting element is functionally connected by a projection from the outer wall section of the outer ring section to same outer wall section. An especially simple, cost-effective and at the same time reliable functional connection is established by such a functional connection between the adjusting element and the HME storage frame. The projection may mesh, for example, with a corresponding mount in the adjusting element or be received lockingly in same. Such a nondestructively detachable connection between the adjusting element and the HME storage frame has the further advantage that the adjusting element can easily be replaced by another adjusting element in case of wear.

Further measures improving the present invention appear from the following description of different exemplary embodiments of the present invention, which are schematically shown in the figures. All the features and/or advantages, including design details and arrangements in space, which appear from the claims, the description or the drawings, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
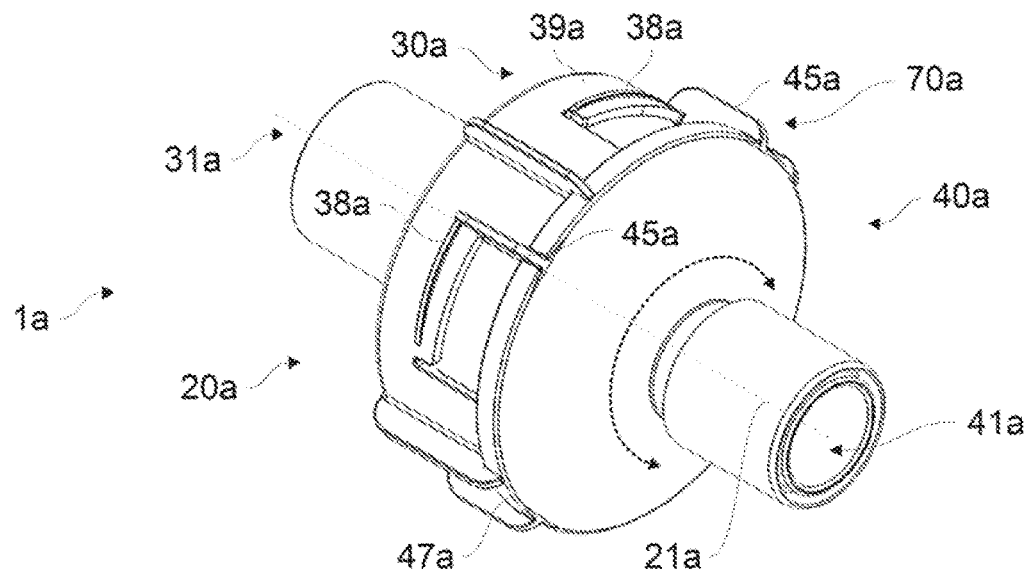
FIG. 1 is a perspective view of an HME device according to a first embodiment of the present invention.
Figure 2:
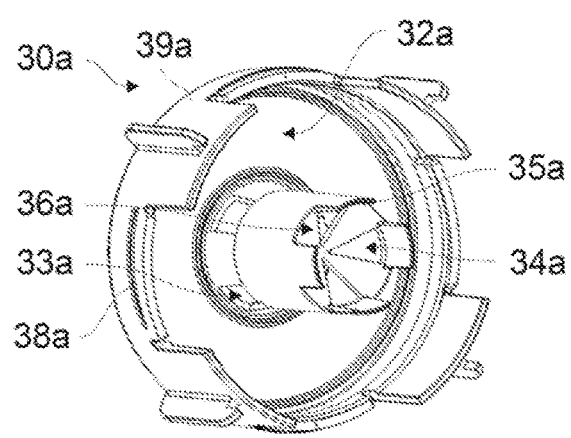
FIG. 2 is a perspective view of an inlet-side housing half of the HME device according to the first embodiment of the present invention.
Figure 3:
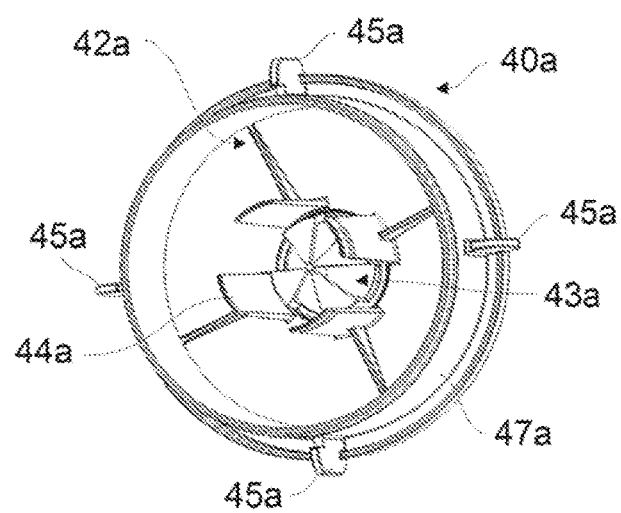
FIG. 3 is a perspective view of an outlet-side housing half of the HME device according to the first embodiment of the present invention.
Figure 4:
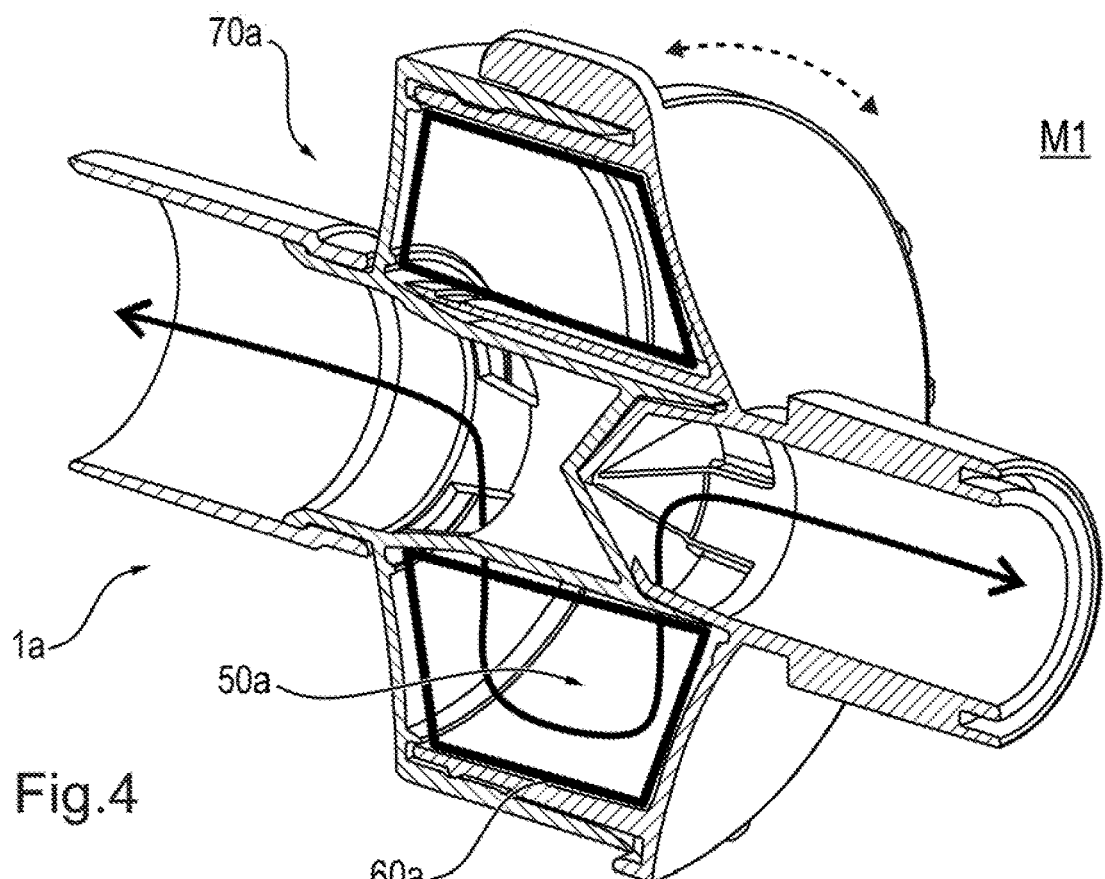
FIG. 4 is a perspective sectional view of the HME device according to the first embodiment of the present invention in an HME mode.
Figure 5:
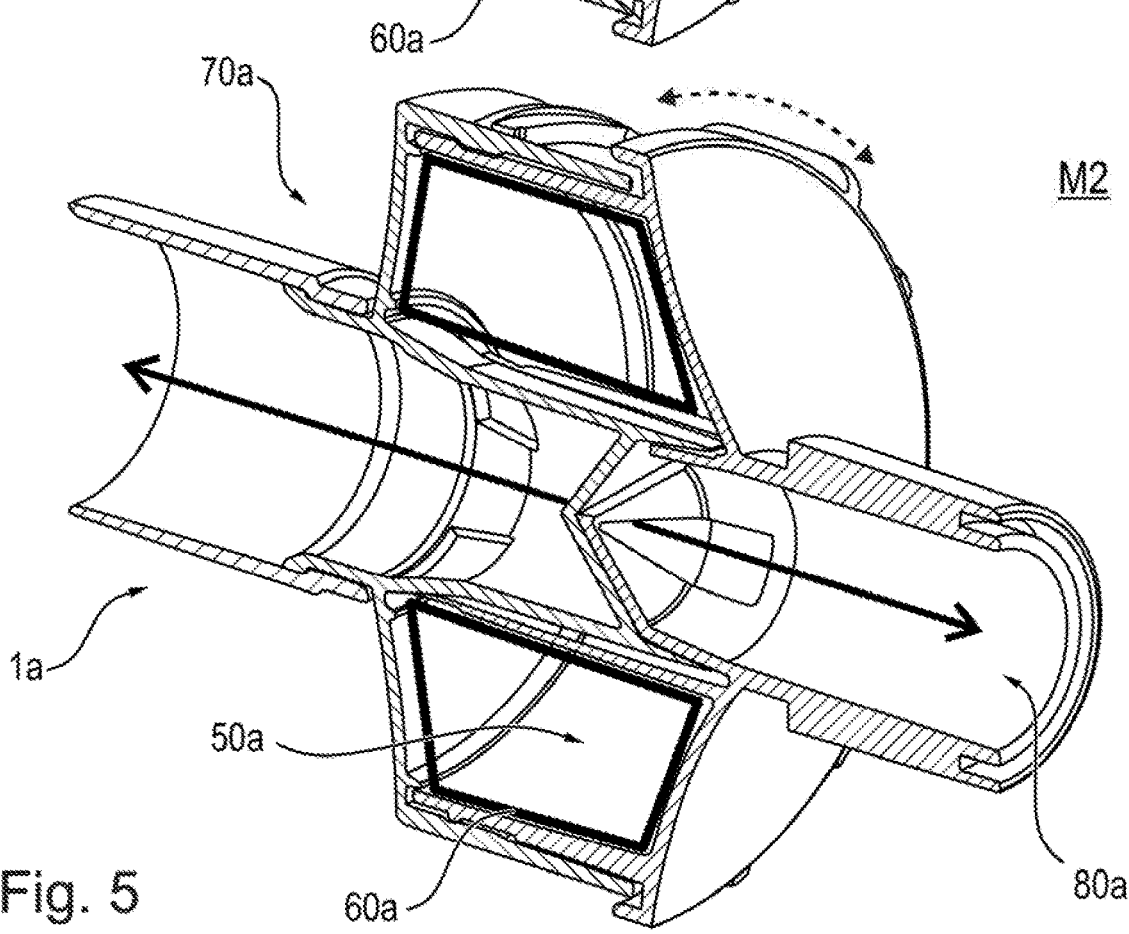
FIG. 5 is a perspective sectional view of the HME device according to the first embodiment of the present invention in a bypass mode.
Figure 6:
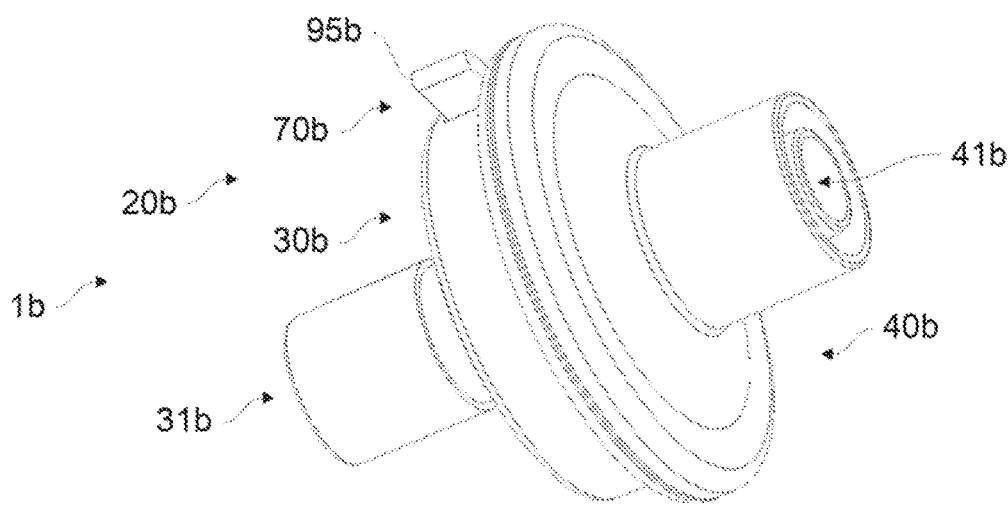
FIG. 6 is a perspective view of the HME device according to a second embodiment of the present invention.
Figure 7:
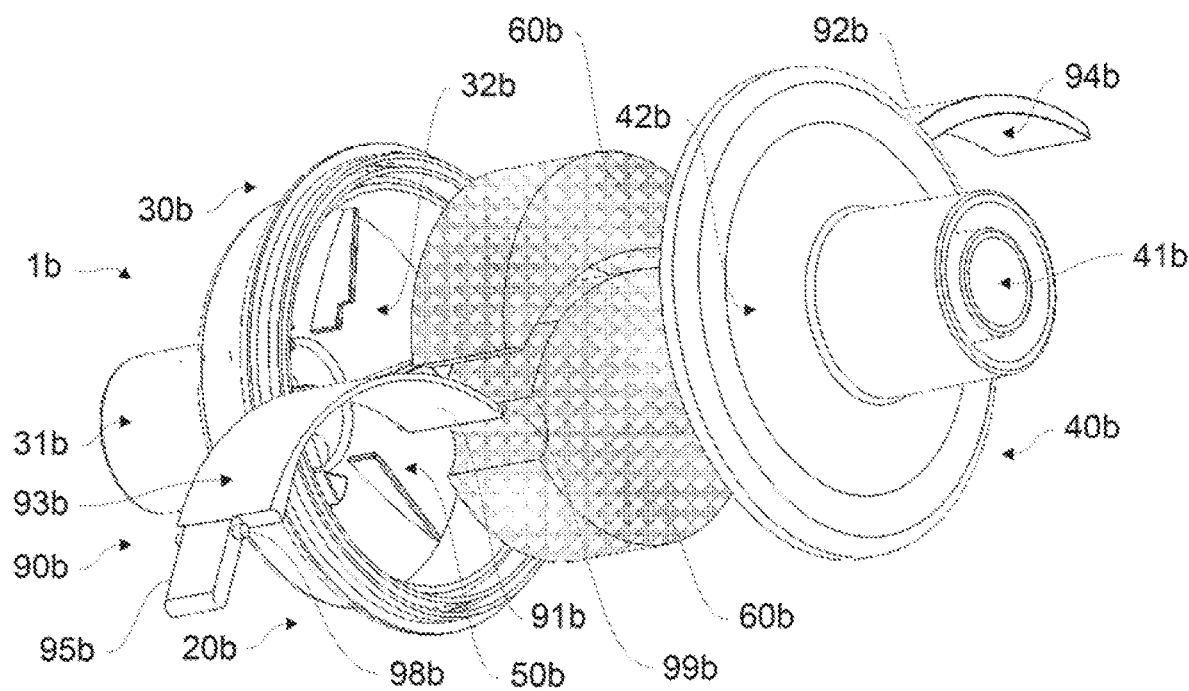
FIG. 7 is an exploded perspective view of the HME device according to the second embodiment of the present invention.
Figure 8:
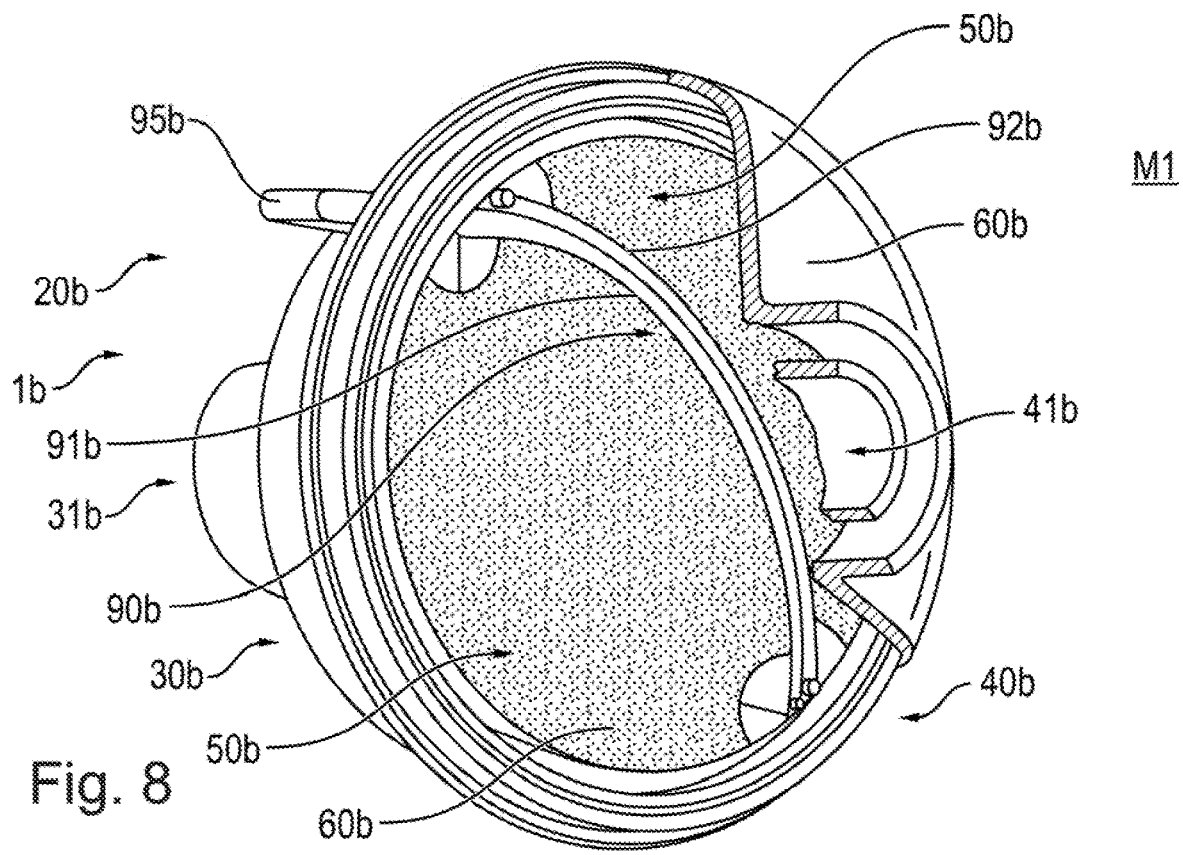
FIG. 8 is a perspective view of the HME device according to the second embodiment of the present invention in an HME mode.

Referring to the drawings, elements with the same function and mode of operation are always designated in FIGS. 1 through 35 by the same or similar reference numbers, which at times differ from one another only by embodiment-specific letters.

Different embodiments of an HME device 1a, 1b, 1c, 1d, 1e, 1f, 1g, 1h, 1i according to the present invention for use in a closed breathing circuit of a ventilation system are shown in FIGS. 1 through 35. The HME device 1a, 1b, 1c, 1d, 1e, 1f, 1g, 1h, 1i shown has a housing 20a, 20b, 20c, 20d, 20e, 20f, 20g, 20h, 20i with an inlet opening 31a, 31b, 31c, 31d, 31e, 31f, 31g, 31h, 31i and with an outlet opening 41a, 41b, 41c, 41d, 41e, 41f, 41g, 41h, 41i. Further, the HME device 1a, 1b, 1c, 1d, 1e, 1f, 1g, 1h, 1i has an HME chamber 50a, 50b, 50c, 50d, 50e, 50f, 50g, 50h, 50i arranged between the inlet opening 31a, 31b, 31c, 31d, 31e, 31f, 31g, 31h, 31i and the outlet opening 41a, 41b, 41c, 41d, 41e, 41f, 41g, 41h, 41i for receiving an HME medium 60a, 60b, 60c, 60d, 60e, 60f, 60g, 60h, 60i, which is configured here as an HME foam element. Moreover, the HME device 1a, 1b, 1c, 1d, 1e, 1f, 1g, 1h, 1i has a switching mechanism 70a, 70b, 70c, 70d, 70e, 70f, 70g, 70h, 70i, by which the HME device 1a, 1b, 1c, 1d, 1e, 1f, 1g, 1h, 1i can be switched between an HME mode M1, in which an HME fluid passage is provided from the inlet opening 31a, 31b, 31c, 31d, 31e, 31f, 31g, 31h, 31i through the HME chamber 50a, 50b, 50c, 50d, 50e, 50f, 50g, 50h, 50i to the outlet opening 41a, 41b, 41c, 41d, 41e, 41f, 41g, 41h, 41i, and a bypass mode M2, in which a fluid bypass passage is provided from the inlet opening 31a, 31b, 31c, 31d, 31e, 31f, 31g, 31h, 31i past the HME chamber 50a, 50b, 50c, 50d, 50e, 50f, 50g, 50h, 50i through a bypass channel 80a, 80b, 80c, 80d, 80e, 80f, 80g, 80h, 80i in the housing 20a, 20b, 20c, 20d, 20e, 20f, 20g, 20h, 20i to the outlet opening 41a, 41b, 41c, 41d, 41e, 41f, 41g, 41h, 41i, wherein the bypass channel 80a, 80b, 80c, 80d, 80e, 80f, 80g, 80h, 80i is blocked in the bypass mode M2 against (with respect to) the HME chamber 50a, 50b, 50c, 50d, 50e, 50f, 50g, 50h, 50i. In other words, the HME medium 60a, 60b, 60c, 60d, 60e, 60f, 60g, 60h, 60i in the HME chamber 50a, 50b, 50c, 50d, 50e, 50f, 50g, 50h, 50i is, in the bypass mode M2, separated at least on the patient side as well as on the ventilator side from the bypass channel 80a, 80b, 80c,

80*d*, 80*e*, 80*f*, 80*g*, 80*h*, 80*i*, as a result of which drug aerosol cannot come into contact with the HME medium 60*a*, 60*b*, 60*c*, 60*d*, 60*e*, 60*f*, 60*g*, 60*h*, 60*i* during the atomization of a drug.

FIGS. 1 through 5 show a first embodiment of the present invention. According to the embodiment shown in FIG. 1, the housing 20*a* has an inlet-side housing half 30*a* with the inlet opening 31*a* and an outlet-side housing half 40*a* with the outlet opening 41*a*. Further, FIG. 1 shows a switching mechanism 70*a*, with which, among other things, turning handles 45*a* and holding elements 48*a* are associated. The outlet-side housing half 40*a* can be rotated by a user in a simple manner against the inlet-side housing half 30*a* by the turning handles 45*a*. The holding elements 38*a* have a convex configuration or are configured as an arched projection at or on an outer wall section of the inlet-side housing half 30*a*. The turning handles 45*a* form a bistable holding mechanism with the holding elements 38*a*, by which holding mechanism intermediate switching states between the HME mode M1 and the bypass mode M2 can be prevented. As soon as one of the turning handles 45*a* is moved over the contour of a corresponding radial holding element 38*a*, a restoring force is generated, which acts up to the point of the greatest deflection of the turning handle 45*a*. If the turning handle 45*a* is now moved beyond this point over the contour of the holding element 38*a*, a force acts in the direction of a switchover motion. Only one of the two intermediate states, i.e., the HME mode M1 or the bypass mode M2, can thus become active, without intermediate switching states being able to be reached. Further, FIG. 1 shows an axis of rotation 21*a*, about which the outlet-side housing half 40*a* is mounted rotatably.

FIG. 2 shows an inlet-side housing half 30*a* in detail. As is shown in FIG. 2, the inlet-side housing half 30*a* has an inner wall section 32*a*. Further, the inlet-side housing half 30*a* has first inlet holes 33*a*, second inlet holes 34*a*, inlet diaphragms 35*a* as well as inlet diaphragm passages 36*a* formed between the inlet diaphragms 35*a*.

FIG. 3 shows the outlet-side housing half 40*a* in detail. According to FIG. 3, the outlet-side housing half 40*a* has an inner wall section 42*a*. In addition, the outlet-side housing half 40*a* has outlet holes 43*a* and outlet diaphragms 44*a*.

The HME device 1*a* is shown in the HME mode M1 in FIG. 4. The HME device is shown in the bypass mode M2 in FIG. 5. Some of the reference numbers are not shown in FIGS. 4 and 5 for the sake of greater clarity.

As is shown in FIG. 4, the HME chamber 50*a* is formed by the first inner wall section 32*a* of the inlet-side housing half 30*a* and by the second inner wall section 42*a* of the outlet-side housing half 40*a*. An inner wall section is defined here especially as a wall section or a wall surface, which wall section or wall surface is formed within an outer wall section 39*a*, 47*a* or an outer wall surface of the housing halves 30*a*, 40*a*. The inlet-side housing half 30*a* and the outlet-side housing half 40*a* are arranged rotatably relative to one another to block and open the bypass channel 80*a*. An HME fluid passage is provided in the HME mode M1 shown in FIG. 4 from the inlet opening 31*a* through the first inlet holes 33*a*, the HME chamber 50*a* and the HME medium 60*a*, the inlet diaphragm passages 36*a* to the outlet opening 41*a*. An HME fluid passage is correspondingly created at the same time from the outlet opening 41*a* through the inlet diaphragm passages 36*a*, the HME medium 60*a*, the HME chamber 50*a* and the first inlet holes 33*a* to the inlet opening 31*a*. The second inlet holes 34*a* are covered in the HME mode M1 by wall sections between the outlet holes 43*a* and the outlet holes 43*a* by wall sections between the second inlet holes 34*a* and the first inlet holes 33*a*, and the inlet diaphragm passages 36*a* are released, i.e., not covered by the outlet diaphragms 44*a*. The HME fluid passage is indicated by a double arrow in FIG. 4.

A fluid bypass passage is provided in the bypass mode M2 shown in FIG. 5 from the inlet opening 31*a* past the HME chamber 50*a* as well as the HME medium 60 through the bypass channel 80*a* and also through the second inlet holes 34*a* and the outlet holes 43*a* to the outlet opening 41*a*. A fluid bypass passage is correspondingly also provided from the outlet opening 41*a* past the HME chamber 50*a* as well as the HME medium 60*a* through the bypass channel 80*a* and also through the outlet holes 43*a* and the second inlet holes 34*a* to the inlet opening 31*a*. The first inlet holes 33*a* and the inlet diaphragm passages 36*a* are covered by the outlet diaphragms 44*a* in the bypass mode M2, and the second inlet holes 34*a* are arranged flush with the outlet holes 43*a*. The fluid bypass passage is indicated by a double arrow in FIG. 5.

FIGS. 6 through 9 show a second embodiment of the present invention. As is shown in FIG. 6, the housing 20*a* of the HME device 1*b* has a first housing half 30*b* with the inlet opening 31*b* and a second housing half 40*b* with the outlet opening 41*b*. Further, the HME device has a switching mechanism 70*b*, which is configured for switching over between the HME mode M1 and the bypass mode M2. Among other things, a manual actuating device 95*b* is associated with the switching mechanism 70*b*.

FIG. 7 shows an exploded view of the HME device 1*b* according to the second embodiment. As is seen in this view, the inlet-side housing half 30*b* has an inner wall section 32*b*. The outlet-side housing half 40*b* likewise has an inner wall section 42*b*, which is shown as being covered in FIG. 7. Further, FIG. 7 shows a sealing element 99*b* and a displacing device 90*b* for displacing the HME medium 60*b* in the HME chamber 50*b* with an outer wall section or with an outer wall surface 91*b*, 92*b*. The HME chamber 50*b* is formed here by the inner wall section 32*b* of the inlet-side housing half 30*b*, the inner wall section of the outlet-side housing half 40*b*, i.e., an inner wall section of the housing 20*b*, and by the outer wall section 91*b*, 92*b* of the displacing device 90*b* of the HME device 1*b*. The displacing device 90*b* is arranged movably for blocking a bypass channel 80*b* in the bypass mode M2 against the HME chamber 50*b*.

The displacing device 90*b* has a plate-shaped first partition section 93*b* and a plate-shaped second partition section 94*b*, an outer wall section 91*b* of the first partition section 93*b* and an outer wall section 92*b* of the second partition section corresponding to or being equivalent to the above-described outer wall section 91*b*, 92*b* of the displacing device 90*b*.

The outer wall section 91*b* or the first partition section 93*b* with the outer wall section 91*b* is elastically deformable for displacing the HME medium 60*b* and/or for blocking the bypass channel 80*b* in the bypass mode M2 against the HME chamber 50*b* and is configured movably relative to the second partition section 94*b*. For a simpler and defined motion and/of deformation of the displacing device 90*b*, this is fixed on or in the hosing 20*b*; 20*c* at four fastening points and by a first coupling element 98*b* and a second coupling element.

The manual actuating device 95*b* configured as a tumbler switch is configured here for moving or elastically deforming the displacing device 90*b* and is a monolithic component thereof.

FIG. 8 shows the HME device 1*b* according to the second embodiment in the HME mode M1. The first partition section 93b and the second partition section 94b are arranged in this state adjoining one another bent from a direct passage area between the inlet opening 31b and the outlet opening 41b. In other words, the two plate-shaped partition sections 93b, 94b are arranged bent in the same first direction in the HME mode M1.

Figure 9:
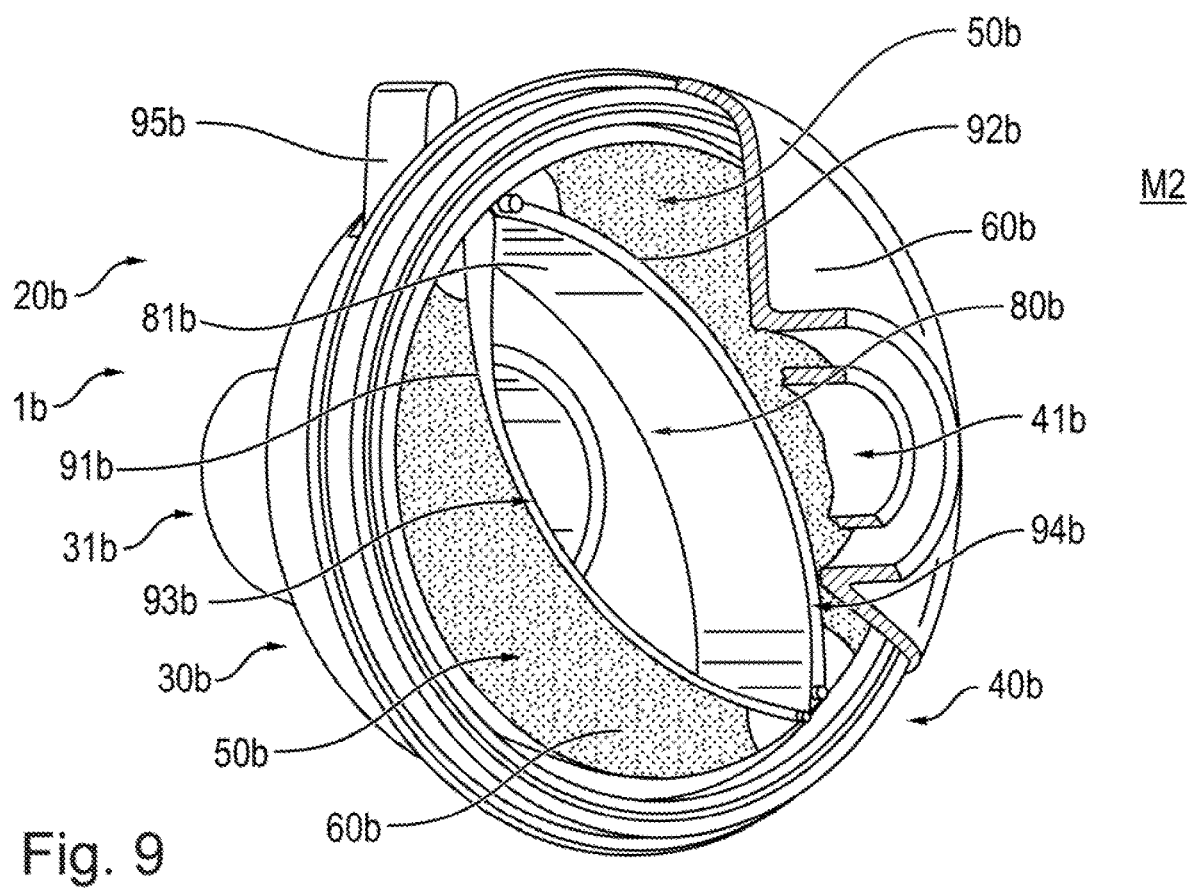
FIG. 9 is a perspective view of the HME device according to the second embodiment of the present invention in a bypass mode.

FIG. 9 shows the HME device 1b in the bypass mode M2. The first partition section 93b is elastically deformed in this state in a second direction, which is opposite the first direction, for displacing the HME medium and for blocking the bypass channel 80b against the HME chamber 50b. The first partition section 93b is arranged and configured here elastically deformably such that this can be deformed in a bistable manner by a residual stress into an HME end position or into a bypass end position. As is also shown in FIG. 9, the two partition sections 93b, 94b have an inner surface each, which correspond to an inner wall section 81b of the bypass channel 80b.

Figure 10:
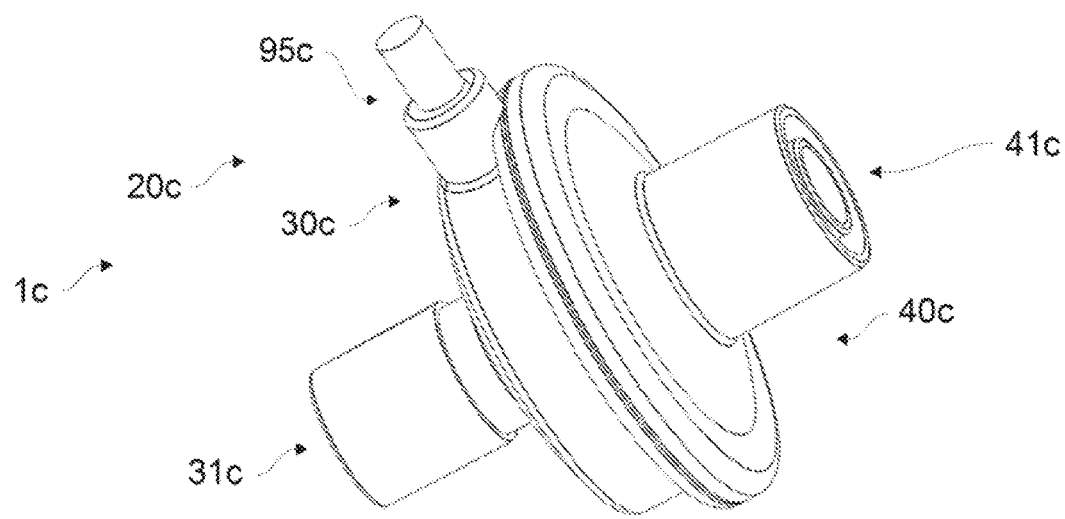
FIG. 10 is a perspective view of the HME device according to a third embodiment of the present invention.
Figure 11:
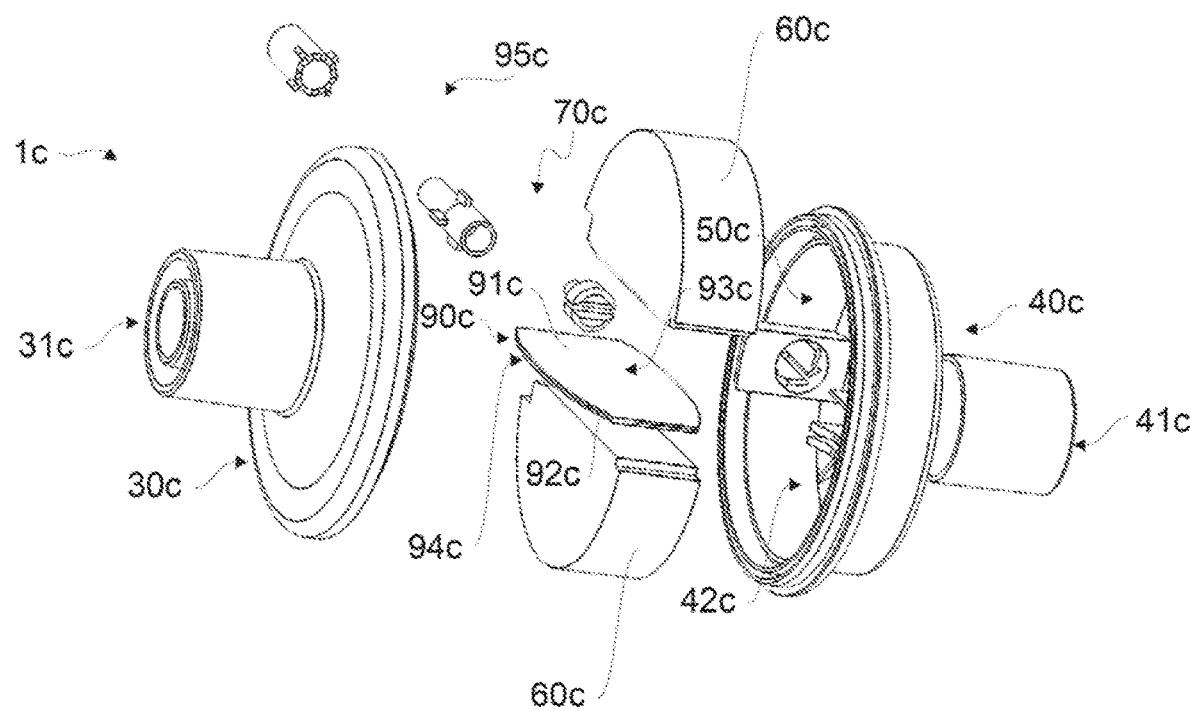
FIG. 11 is an exploded perspective view of the HME device according to the third embodiment of the present invention.
Figure 12:
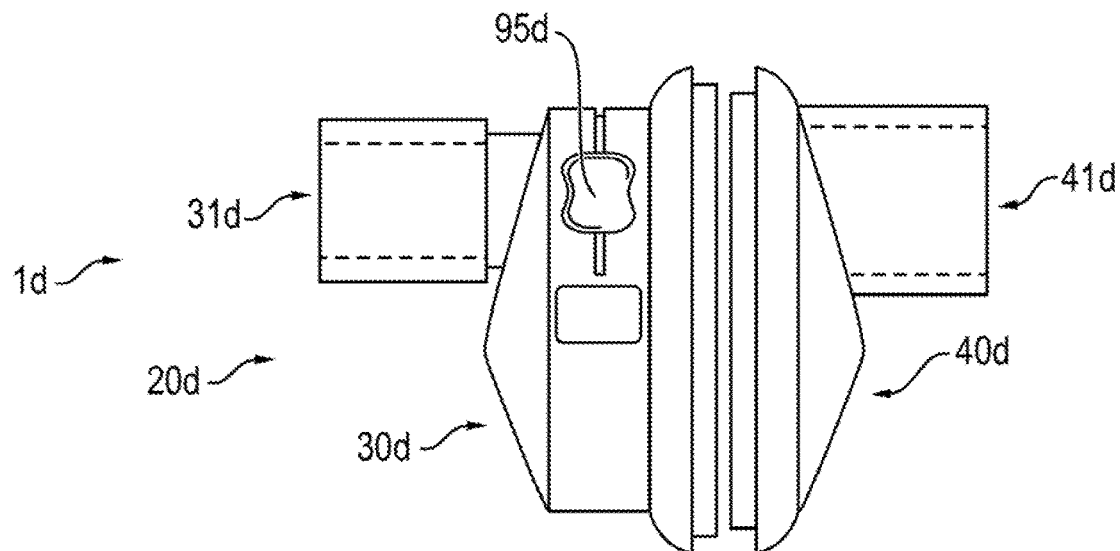
FIG. 12 is a side view of the HME device according to a fourth embodiment of the present invention.

FIGS. 10 and 11 show a third embodiment of the present invention. The housing 20c of the HME device 1c shown in FIG. 10 has an inlet-side housing half 30c with the inlet opening 31c and an outlet-side housing half 40c with the outlet opening 41c. The HME device 1c in FIG. 10 has, further, a manual actuating device 95c. The manual actuating device 95c has a lifting and rotating mechanical that can be actuated by pressing for moving and/or elastically deforming a displacing device 90b, 90c as is described above or, according to the third embodiment, at least one of the two plate-shaped partition sections 93b, 94b and 93c, 94c, respectively. The lifting and rotating mechanism is configured as a "clicker" or "retractable ballpoint pen mechanism" known from the state of the art and it will not therefore be explained here in more detail.

FIG. 11 shows an exploded view of the HME device 1c according to the third embodiment. According to FIG. 11, the HME device 1c has, further, a switching mechanism 70c, with which both the displacing device 90c and the manual actuating device 95c are associated. The displacing device 90c has, according to FIG. 11, an outer wall section 91c of a first partition section 93c and an outer wall section 92c of a second partition section 94c. Further, FIG. 11 shows an HME medium 60c, which can be arranged in an HME chamber 50c. The HME chamber 50c is formed according to the third embodiment shown in FIG. 11 by an inner wall section 42c of the housing 20c or an inner wall section of the inlet-side housing half 30c and by an inner wall section 42c of the outlet-side housing half 40c as well as by the outer wall section 91c, 92c of the displacing device 90c.

FIGS. 12 through 16 show a fourth embodiment of the present invention. The HME device 1d shown in FIG. 12 has an inlet-side housing half 30d with the inlet opening 31d and an outlet-side housing half 40d with the outlet opening 41d. In addition, the HME device has a manual actuating device 95d configured as a radial slide.

Figure 13:
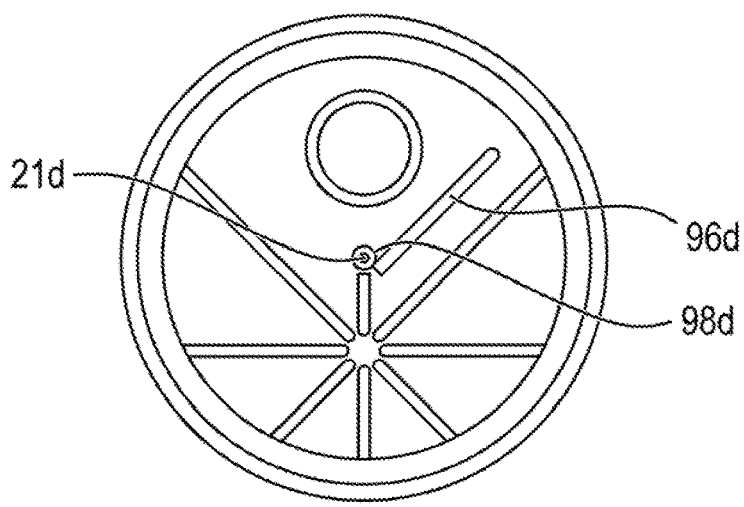
FIG. 13 is a front view of an opened HME device according to the fourth embodiment of the present invention.
Figure 14:
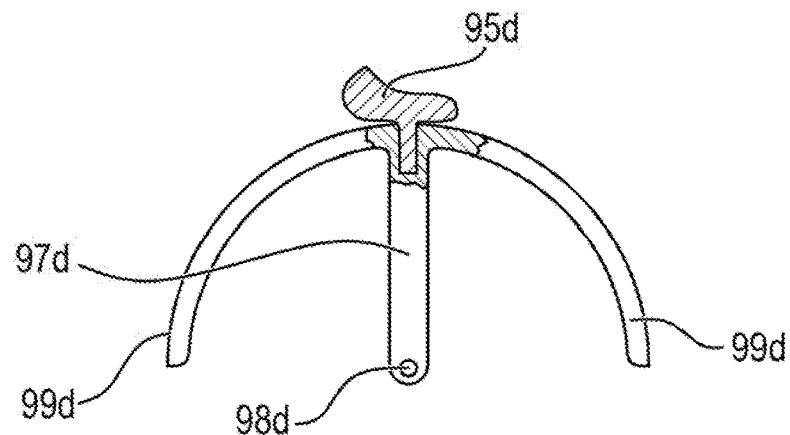
FIG. 14 is a front view of a separating device of the HME device according to the fourth embodiment of the present invention.

FIG. 13 shows a separating device 96d fastened in the housing 20d, for example, on an HME storage frame. In addition, FIG. 13 shows a coupling element 98d, by which an additional separating device 97d, pivotable about an axis of rotation 21d, can be arranged in the housing 20d. This pivotable separating device 97d is shown in FIG. 14. The pivotable separating device 97d has two arm sections, which act as a sealing element 99d for a sealing action between the HME chamber 50d and the bypass channel 80d in the bypass mode M2. As is also shown in FIG. 13, the manual actuating device 95d is permanently connected to the pivotable separating device 97d. More precisely, the manual actuating device 95d shown in FIG. 13 is arranged, in at least some sections, displaceably outside the housing 20d in the circumferential direction of the housing 20d for pivoting the movable separating device 97d.

Figure 15:
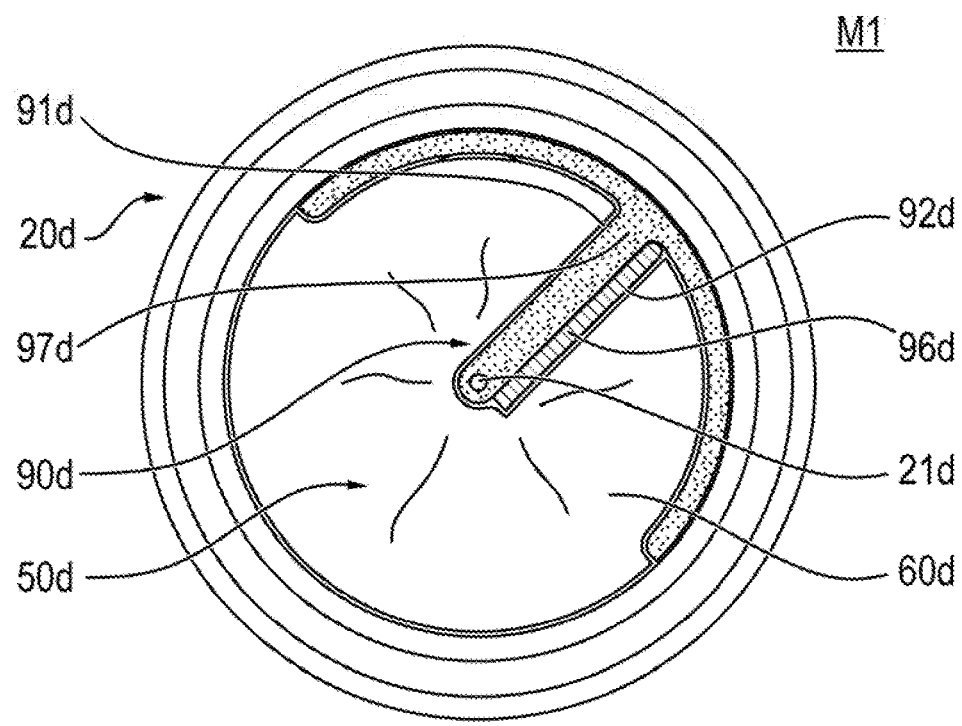
FIG. 15 is a front view of an opened HME device according to the fourth embodiment of the present invention in an HME mode.
Figure 16:
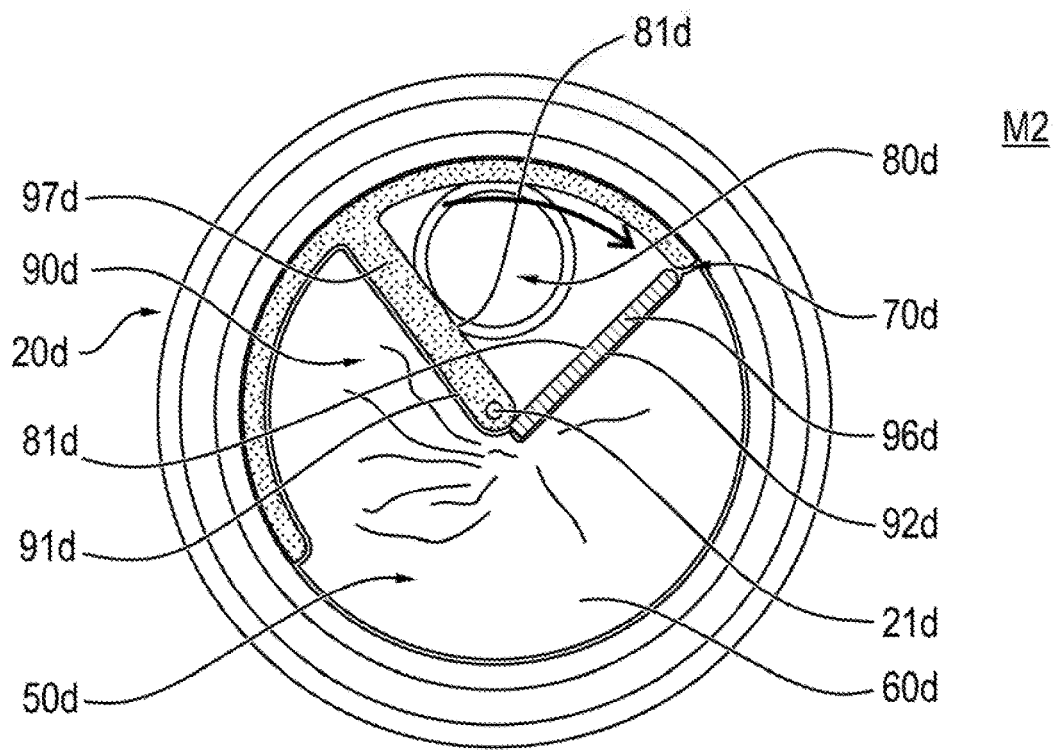
FIG. 16 is a front view of the opened HME device according to the fourth embodiment of the present invention in a bypass mode.

As is shown in FIG. 15 and FIG. 16, the HME chamber 50d is formed by an inner wall section of the housing 20d and by an outer wall section 91d, 92d of a displacing device 90d of the HME device 1d for displacing the HME medium 60d. The displacing device 90d is arranged movably for blocking the bypass channel 80d in the bypass mode M2 against the HME chamber 50d. In addition, the displacing device 90d has, according to the fourth embodiment, the stationary separating device 96d and the pivotable separating device 97d. Further, the stationary separating device 96d and the movable separating device 97d have each an outer wall surface and an inner wall surface, wherein the outer wall surfaces correspond to the outer wall section 91d, 92d of the displacing device 90d and the inner wall surfaces correspond to an inner wall section 81d of the bypass channel 80d. FIG. 15 shows the HME device 1d according to the fourth embodiment in an HME mode M1. The bypass channel 80d is closed in this state by the stationary separating device 96d and the pivotable separating device 97d being located in contact with one another or is not formed. FIG. 16 shows the HME device 1d according to the fourth embodiment in a bypass mode M2. A bypass channel 80d is provided in the bypass mode M2 with a fluid bypass passage in the HME device 1d. The HME device 1d has, further, a switching mechanism 70d according to FIG. 16.

Figure 17:
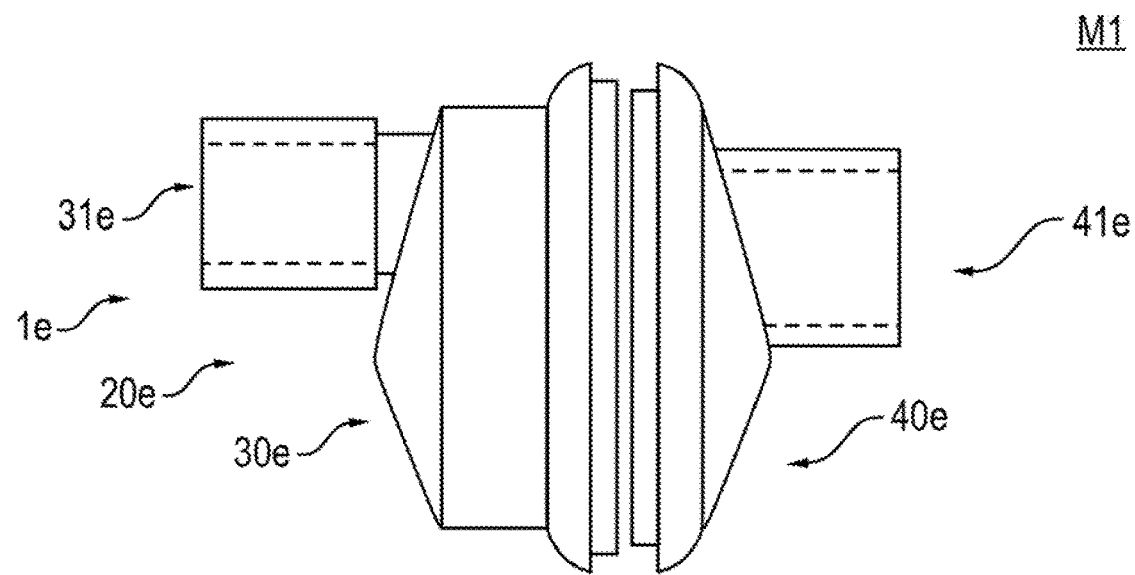
FIG. 17 is a side view of the HME device according to a fifth embodiment of the present invention in an HME mode.
Figure 18:
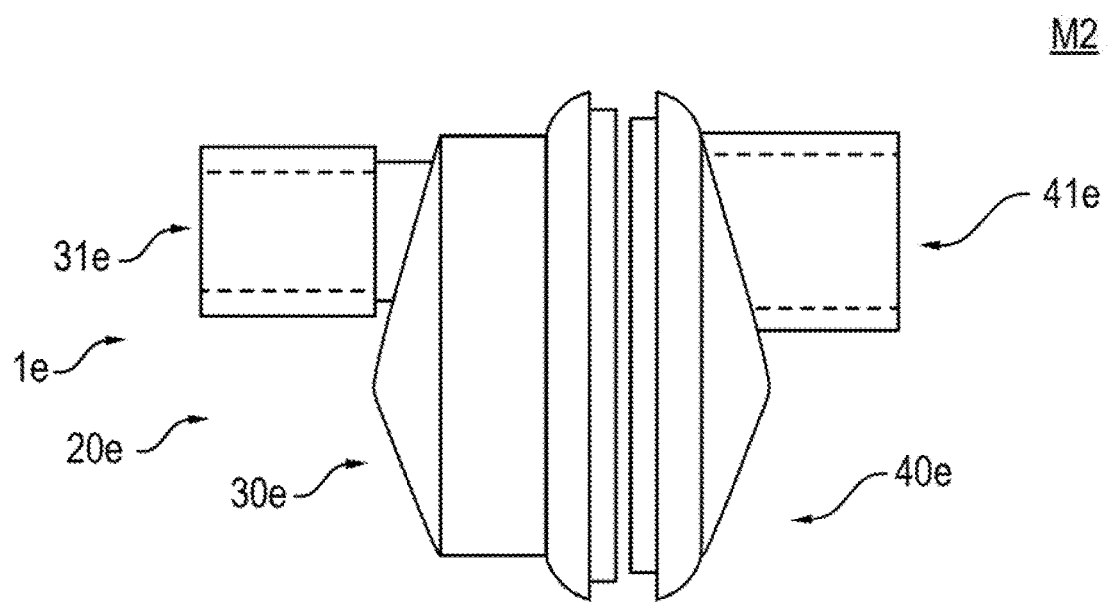
FIG. 18 is a side view of the HME device according to the fifth embodiment of the present invention in a bypass mode.

FIGS. 17 through 20 show a fifth embodiment of the present invention. The HME device 1e shown in FIG. 17 has an inlet-side housing half 30e with the inlet opening 31e and an outlet-side housing half 40e with the outlet opening 41e. FIG. 17 shows the HME device 1e in the HME mode M1. FIG. 18 shows the HME device 1e in the bypass mode M2. To switch over between the HME mode M1 and the bypass mode M2, the inlet-side housing half 30a and the outlet-side housing half 40e are arranged rotatably by about 30° in relation to one another for blocking and opening a bypass channel 80e.

Figure 19:
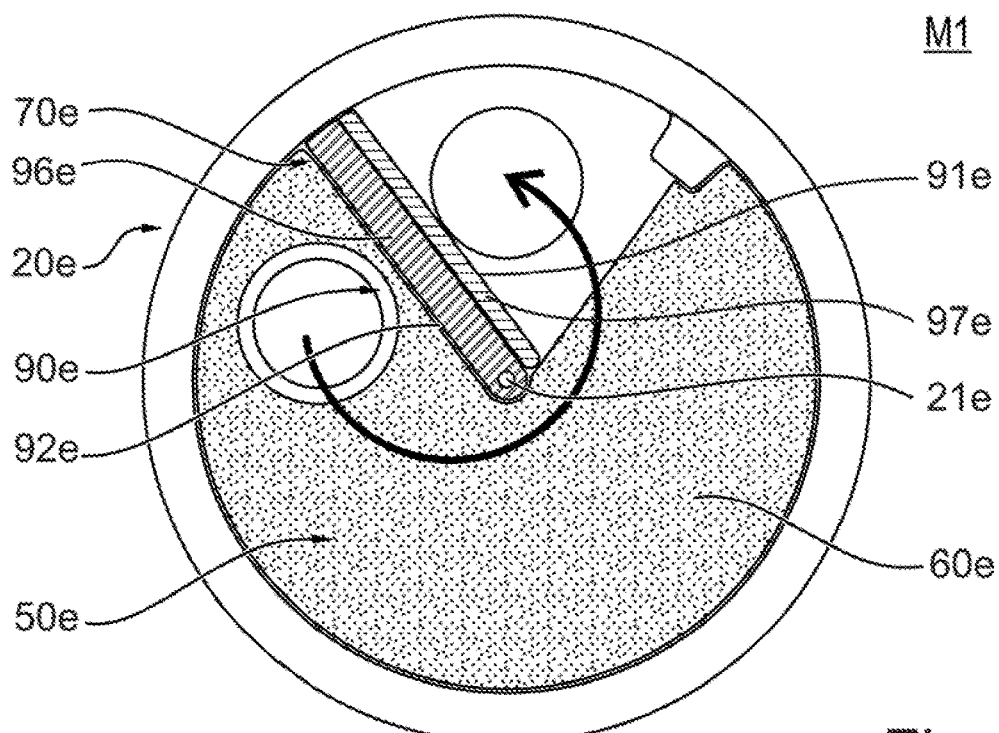
FIG. 19 is a front view of an opened HME device according to the fifth embodiment of the present invention in the HME mode.
Figure 20:
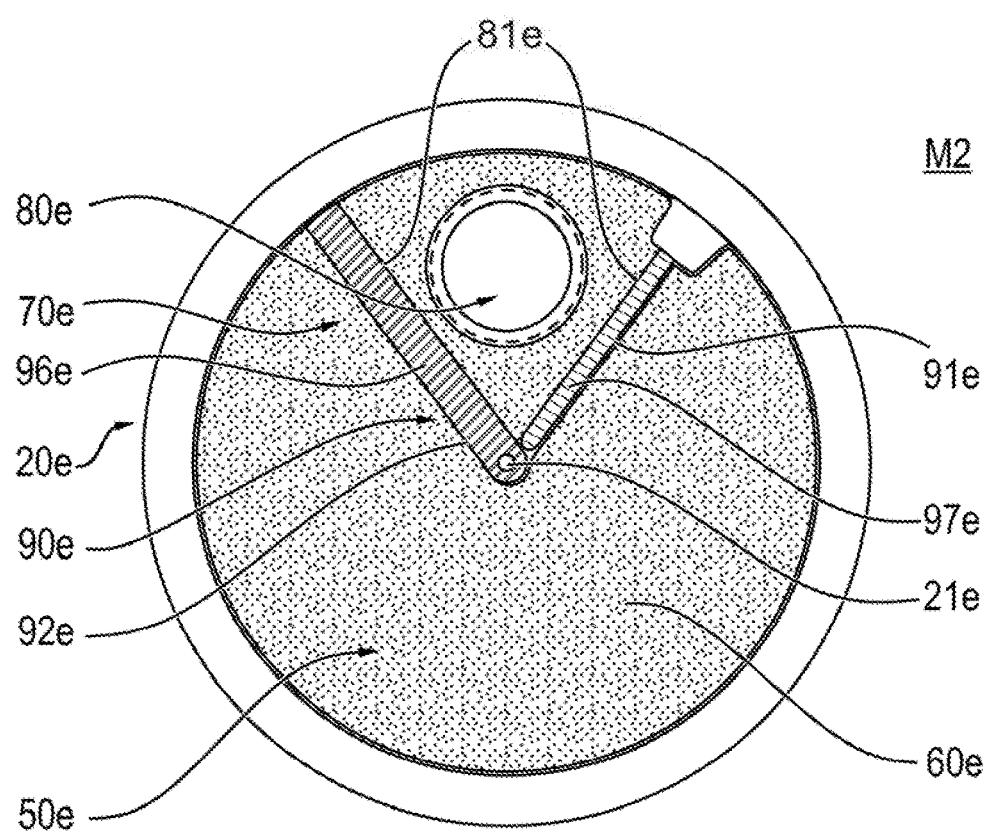
FIG. 20 is a front view of the opened HME device according to the fifth embodiment of the present invention in the bypass mode.

As is shown in FIG. 19 and FIG. 20, the HME chamber 50e of the HME device 1e is formed by a first inner wall section of the inlet-side housing half 30e, a second inner wall section of the outlet-side housing half 30e and an outer wall section 91e, 92e of a displacing device 90e of the HME device 1e for displacing the HME medium 60e. The displacing device 90e has a first separating device 96e and a second separating device 97e for blocking the bypass channel 80e in the bypass mode M2 against the HME chamber 50e, the first separating device 90e and the second separating device 97e being arranged pivotably relative to one another by rotating the housing halves 30e, 40e about the axis of rotation 21e. The first separating device 96e is in functional connection here with the inlet-side housing half 30e and the second separating device 97e is in a functional connection with the outlet-side housing half 40e. Further, the HME device 1e has, according to FIG. 19 and FIG. 20, a switching mechanism 70e.

The first separating device 96e and the second separating device 97e have each an outer wall surface and an inner wall surface, the outer wall surfaces corresponding to the outer wall section 91e, 92e and the inner wall surfaces corresponding to an inner wall section 81e of the bypass channel 80e.

FIGS. 21 through 24 show a sixth embodiment of the present invention. The HME device if shown in FIG. 21 has an inlet-side housing half 30f with the inlet opening 31f and an outlet-side housing half 40f with the outlet opening 41f. Further, the HME device 1f shown in FIG. 21 has a housing window 24*f*, through which an outer wall section or an outer wall surface of a hollow section 100*f* arranged in the housing 20*f* is exposed to the outside.

Figure 21:
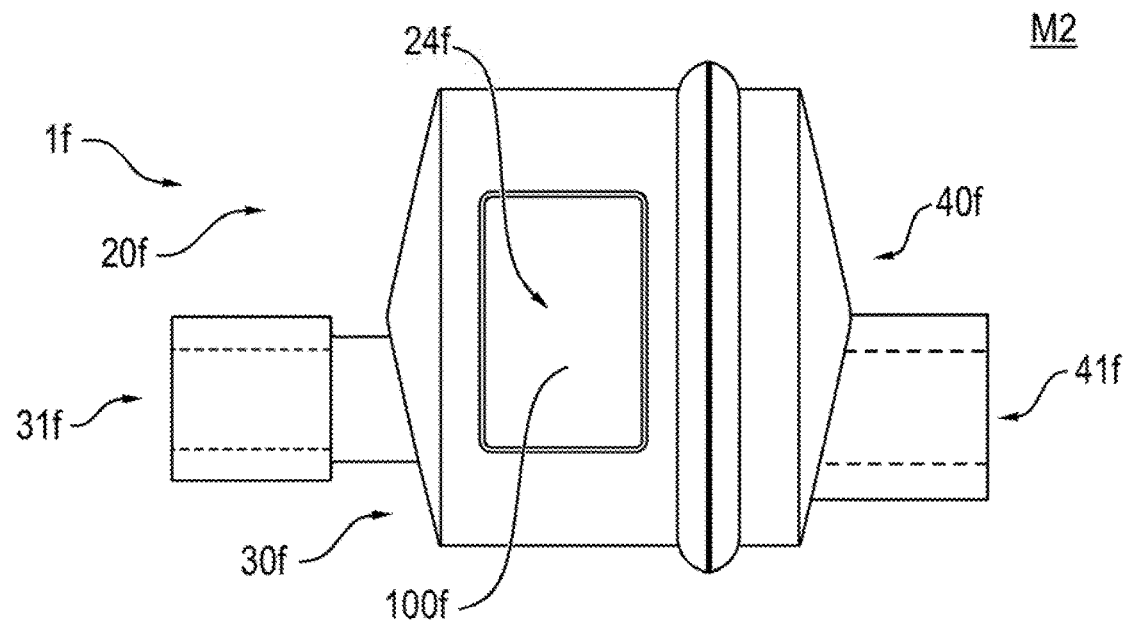
FIG. 21 is a side view of the HME device according to a sixth embodiment of the present invention in a bypass mode.
Figure 22:
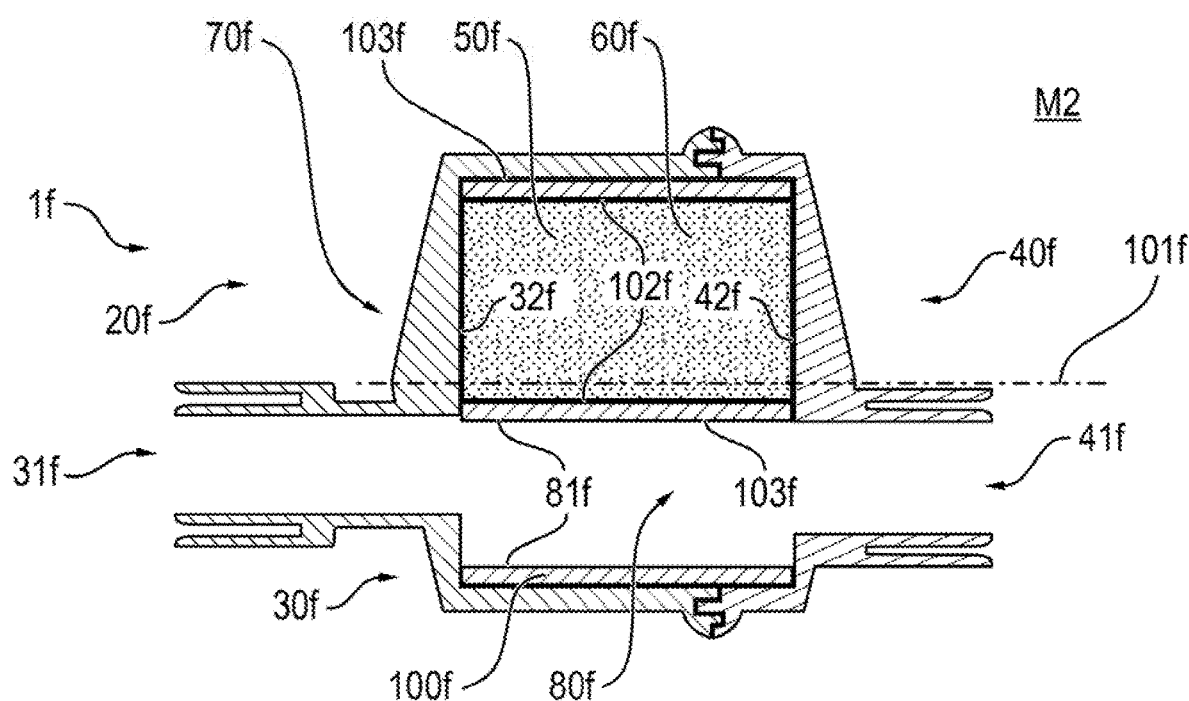
FIG. 22 is a sectional side view of the HME device according to the sixth embodiment of the present invention in the bypass mode.

FIG. 21 as well as well FIG. 22 show the HME device 1*f* in the bypass mode M2. As is shown especially in the sectional view in FIG. 22, the hollow section 100*f* is arranged rotatably about an axis of rotation 101*f* in the housing 20*f*, and an inner wall section of the HME chamber 50*f* corresponds to an inner wall section 102*f* of the hollow section 100E A section of the bypass channel 80*f* can be established between a first outer wall section 103*f* of the hollow section 100*f* and a first inner wall section 22*f* of the housing 20*f*, and the first outer wall section 103*f* of the hollow section 100*f* corresponds to an inner wall section 81*f* of the bypass channel 80*f* or to this.

As it appears, further, from FIG. 22, the HME chamber 50*f* is formed by an inner wall section 102*f* of the hollow section 100*f* and by an inner wall section 32*f*, 42*f* of the housing 20*f* or of the respective housing half 30*f*, 40E The HME device 1*f* has, further, according to FIG. 22, a switching mechanism 70*f*.

Figure 23:
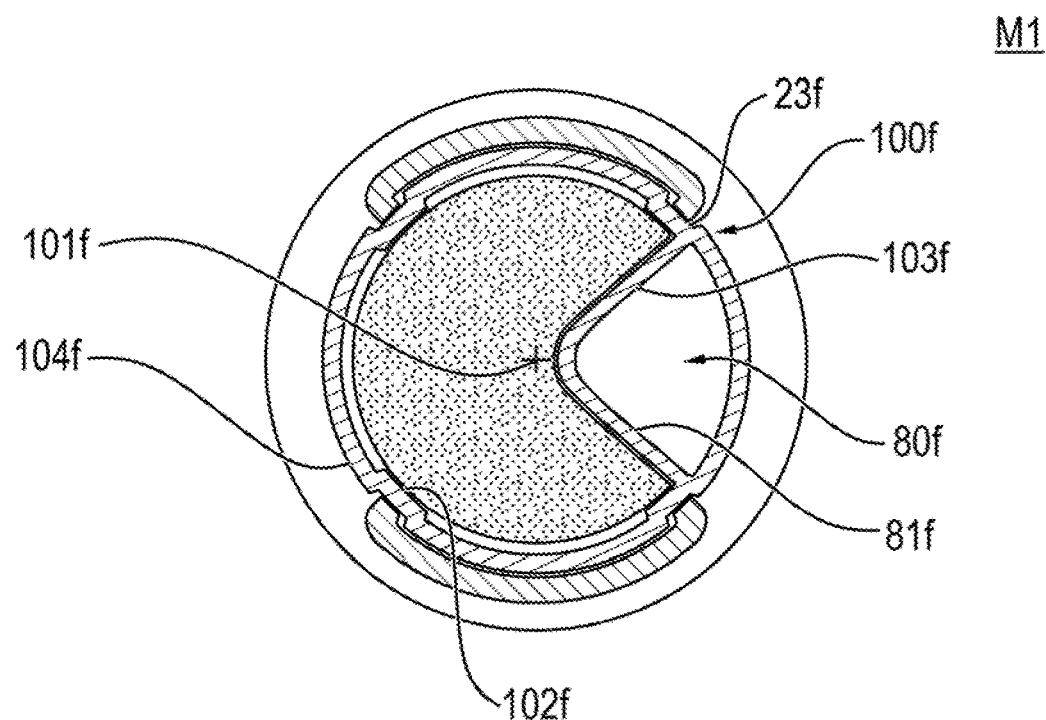
FIG. 23 is a front view of an opened HME device according to the sixth embodiment of the present invention in the HME mode.
Figure 24:
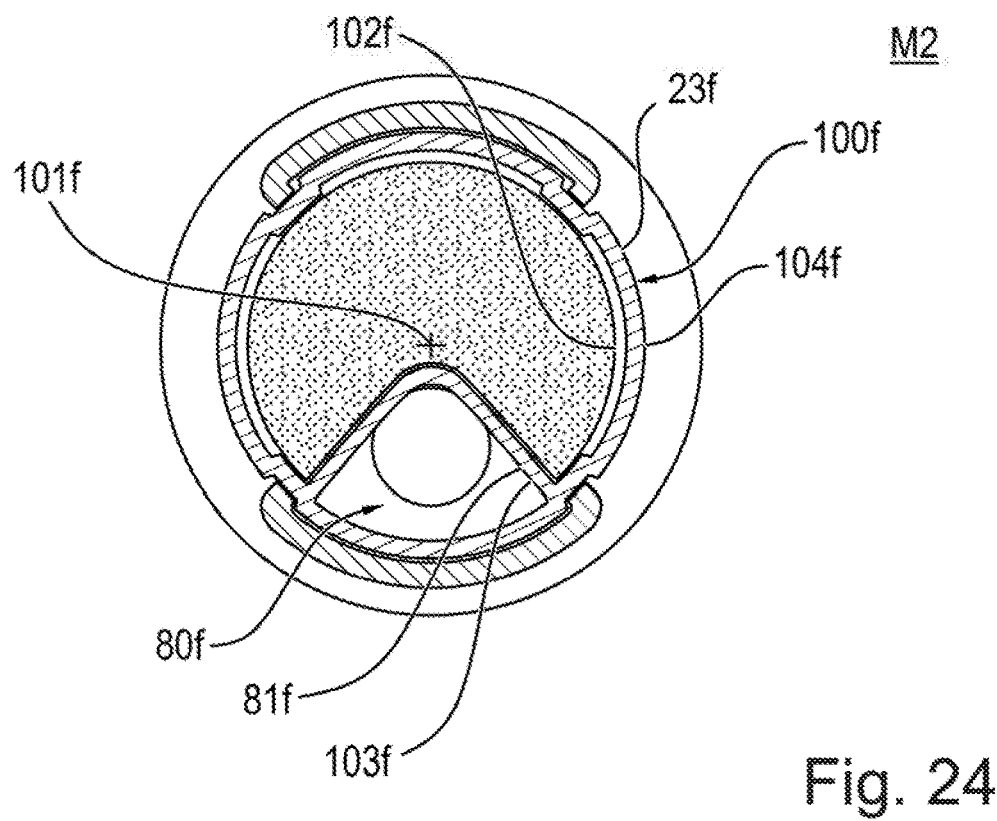
FIG. 24 is a front view of the opened HME device according to the sixth embodiment of the present invention in the bypass mode.

FIG. 23 shows the HME device 1*f* in the HME mode M1, in which the hollow section is arranged rotated in the housing 20*f* such that an HME fluid passage is formed. FIG. 24 shows the HME device 1*f* in the bypass mode M2, in which the first outer wall section 103*f* of the hollow section 100*f* corresponds to an inner wall section 81*f* of the bypass channel 80*f* or is equivalent thereto. In addition, FIG. 23 as well as FIG. 24 show that a second outer wall section 104*f* of the hollow section 100*f* is in flush-integrated contact with a second inner wall section 23*f* of the housing 20*f*.

Figure 25:
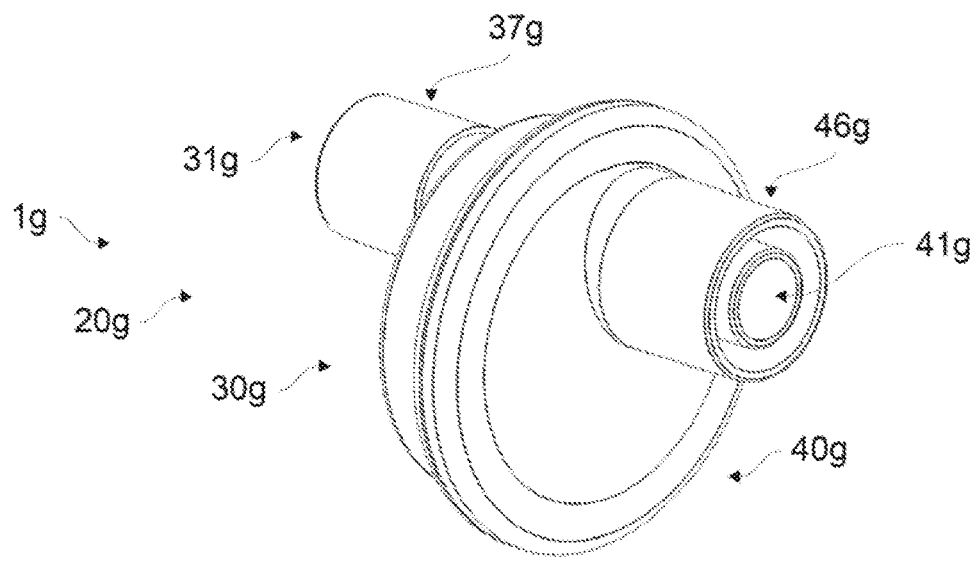
FIG. 25 is a perspective view of the HME device according to a seventh embodiment of the present invention.
Figure 26:
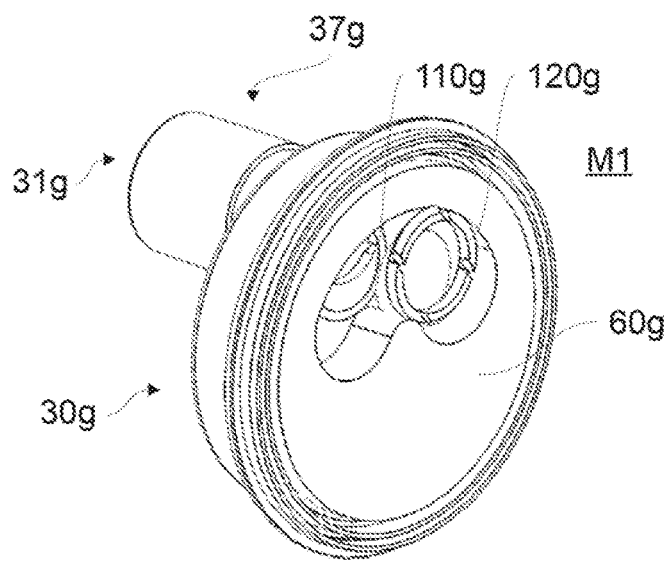
FIG. 26 is a partial perspective view of the HME device according to the seventh embodiment of the present invention.
Figure 27:
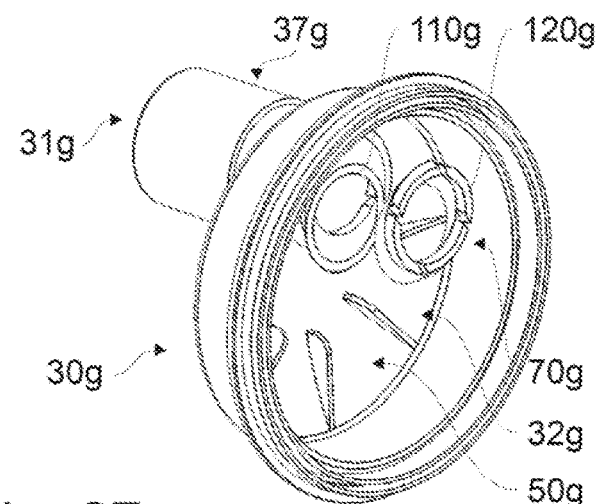
FIG. 27 is another partial perspective view of the HME device according to the seventh embodiment of the present invention.

FIGS. 25 through 27 show a seventh embodiment of the present invention. FIG. 25 shows an HME device 1*g*, in which the housing 20*g* has an inlet-side housing half 30*g* with the inlet opening 31*g* and an outlet-side housing half 40*g* with the outlet opening 41*g*. As is seen especially in FIG. 27, the HME chamber 50*g* for the HME medium 60*g* is formed by a first inner wall section 32*g* of the inlet-side housing half 30*g* and by a second inner wall section of the outlet-side housing half 40*g*. The inlet-side housing half 30*g* and the outlet-side housing half 40*g* are arranged rotated relative to one another for blocking and opening the bypass channel. Further, FIG. 27 shows a switchover mechanism 70*g*.

As is shown, further, in FIGS. 25 through 27, the housing 20*g* has a fluid inlet channel 37*g* and a fluid outlet channel 46*g*, wherein the fluid inlet channel 37*g* is connected to a first fluid switchover channel 110*g* and the fluid outlet channel 46*g* is connected to a second fluid switchover channel 120*g*, wherein the first fluid switchover channel 110*g* extends at right angles to the fluid inlet channel 37*g* and the second fluid switchover channel 120*g* extends at right angles to the fluid outlet channel 46*g*. According to the seventh embodiment, the fluid inlet channel 37*g*, the first fluid switchover channel 110*g*, the second fluid switchover channel 46*g* and the fluid outlet channel 46*g* correspond in some sections to the bypass channel in the bypass mode M2 (not shown). As can be seen in FIGS. 25 through 27, the first fluid switchover channel 110*g* and the second fluid switchover channel 120*g* are configured and can be switched over or rotated such that a flat connection can be established in the bypass mode between the ring-shaped end face of the first fluid switchover channel 110*g* and the ring-shaped end face of the second fluid switchover channel 110*g*, i.e., the first fluid switchover channel 110*g* and the second fluid switchover channel 120*g* or the respective end faces thereof adjoin each other in a fluid-tight, flush-integrated manner and provide a fluid bypass channel according to the present invention as a result.

As is shown in FIG. 26 and FIG. 27, the first fluid switchover channel 110*g* and the second fluid switchover channel 120 *g* are arranged in parallel or essentially in parallel to one another in at least some sections in the HME mode M1.

As is shown by a closer scrutiny of FIG. 26, the HME medium 60*g* in the HME chamber 50*g* has a stepped passage channel 61*g*, in which the fluid outlet channel 120*g* is arranged displaceably and the fluid inlet channel 110*g* is arranged in a positive-locking manner with the HME medium 60*g* on the circumferential side.

Figure 28:
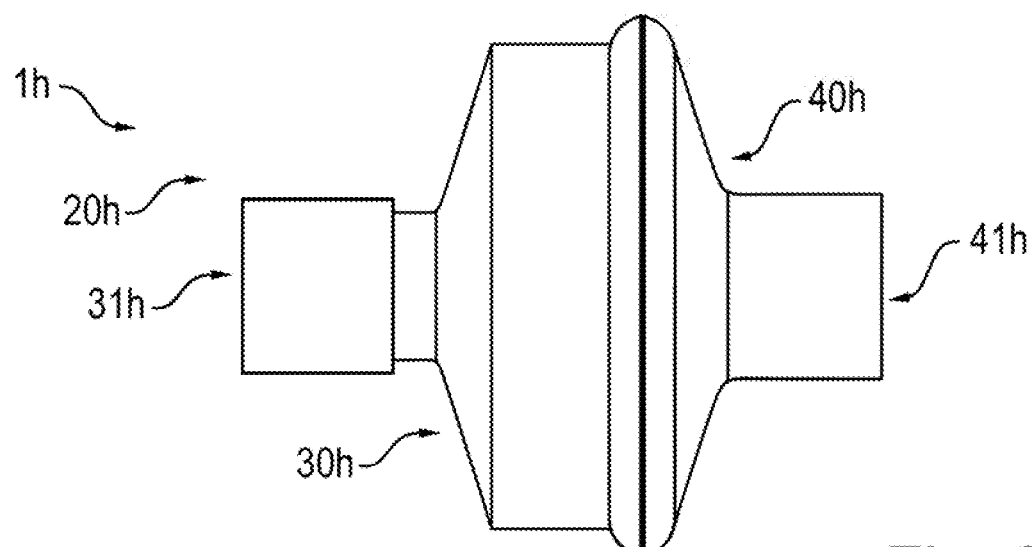
FIG. 28 is a side view of the HME device according to an eighth embodiment of the present invention in a bypass mode.

FIGS. 28 through 31 show an eighth embodiment of the present invention. FIG. 28 shows an HME device 1*h*, in which the housing 20*h* has an inlet-side housing half 30*h* with the inlet opening 31*h* and an outlet-side housing half 40*h* with the outlet opening 41*h*.

Figure 29:
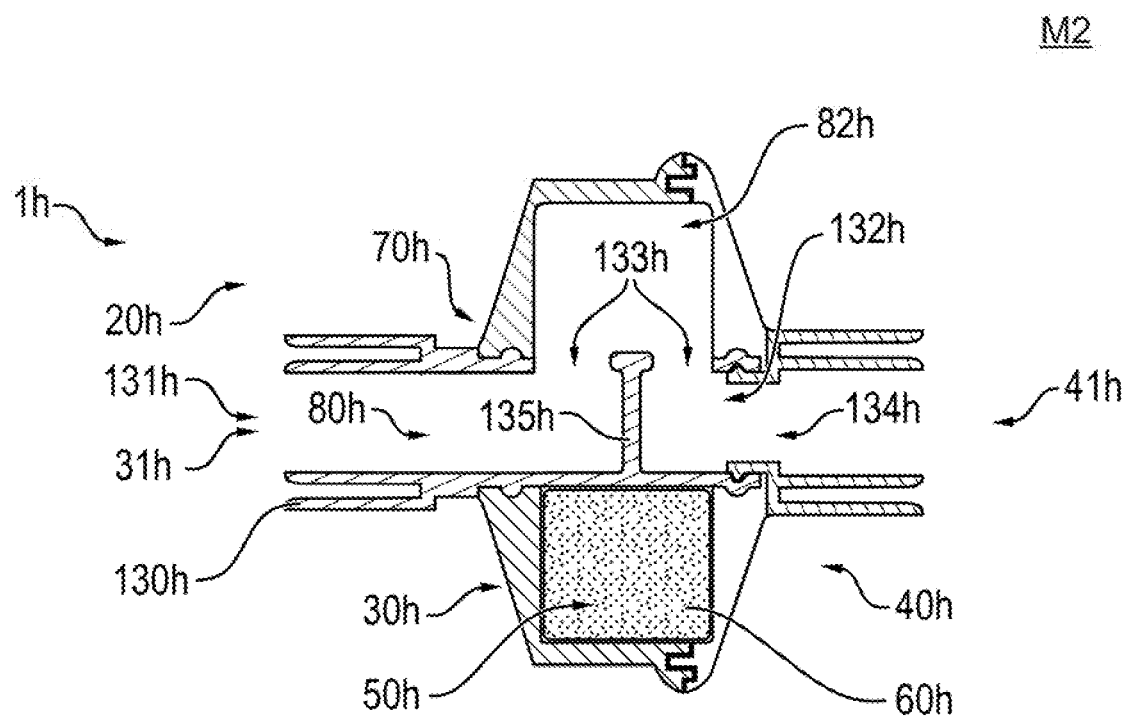
FIG. 29 is a sectional side view of the HME device according to the eighth embodiment of the present invention in the bypass mode.

FIG. 29 shows a sectional side view of the HME device 1*h* according to an eighth embodiment with the switching mechanism 70*h*. As is shown in FIG. 29, a fluid inlet channel 130*h* is arranged in the inlet-side housing half 30*h*, the fluid inlet channel 130*h* and the inlet-side housing half 30*h* being arranged rotatably in relation to one another. In addition, the inlet fluid channel 130*h* has an inlet opening 131*h*, which corresponds to the inlet opening 31*h* of the HME device 1*h* and corresponds to it, and a passage opening 132*h*. As is also shown in FIG. 29, the passage opening 132*h* is directed into the bypass channel 80*h* and a bypass channel 82*h* in the bypass mode M2. The arrangement of the bypass chamber 82*h* and of the HME chamber 80*h* are transposed in the HME mode (not shown), as a result of which the passage opening 132*h* of the non-rotated or moved fluid inlet area 130*h* is directed in this case into the HME chamber 50*h*.

In addition, the passage opening 132*h* has, according to FIG. 29, a lateral opening section 133*h* and a frontal opening section 134*h*, wherein the opening direction of the lateral opening section 133*h* is directed perpendicularly to the opening direction of the inlet opening 131*h* and of the frontal opening section 134*h*. In addition, FIG. 29 shows that the fluid inlet channel 130*h* has a wall section 135*h* that is arranged flush with the lateral opening section 133*h* in the fluid inlet channel 130*h* in parallel to the opening direction of the lateral opening section 133*h*. The wall section 135*h* has a height that corresponds to the passage level of the fluid inlet channel 130 at the location of the wall section 135*h* and corresponds to an average passage level of the fluid inlet channel 130 at the site of the wall section 135*h* and also corresponds to a mean passage level of the fluid inlet channel 130.

Figure 30:
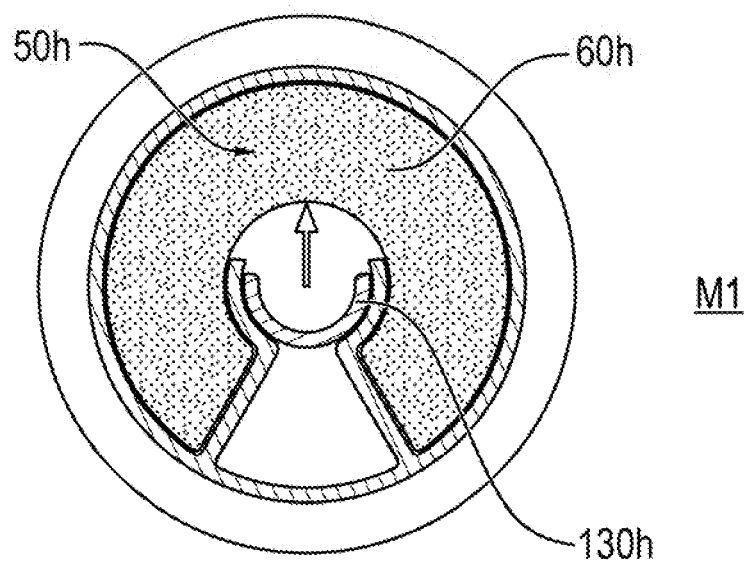
FIG. 30 is a front view of an opened HME device according to the eighth embodiment of the present invention in the HME mode.
Figure 31:
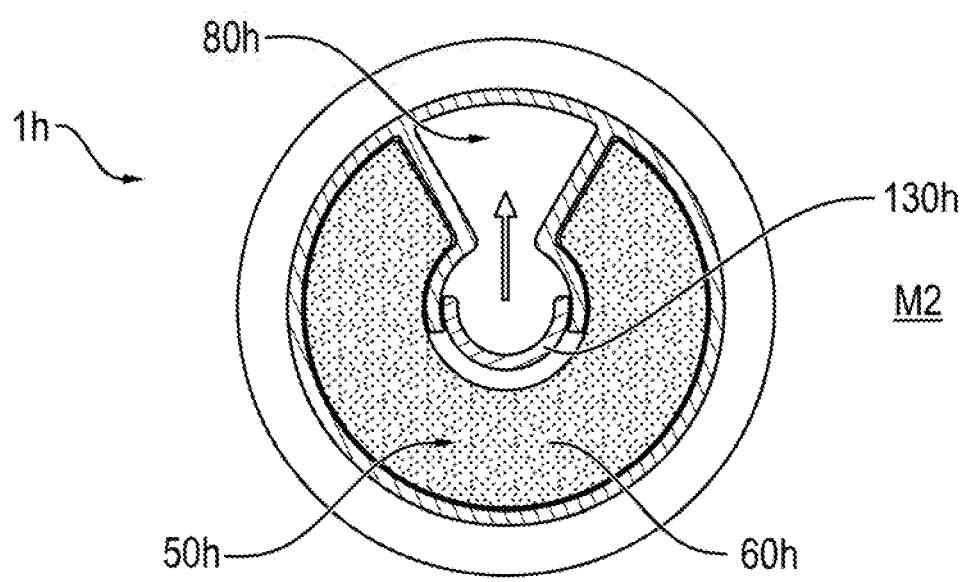
FIG. 31 is a front view of the opened HME device according to the eighth embodiment of the present invention in the bypass mode.

FIG. 30 shows the HME device 1*h* in the HME mode M1, in which the HME fluid passage is provided by the HME medium 60*h* in the HME chamber 50*h*. FIG. 31 shows the HME device 1*h* in the bypass mode M2, in which the fluid bypass passage is provided by the inlet opening 31*h* past the HME medium 60*h* in the HME chamber 50*h* to the outlet opening 41*h*.

Figure 32:
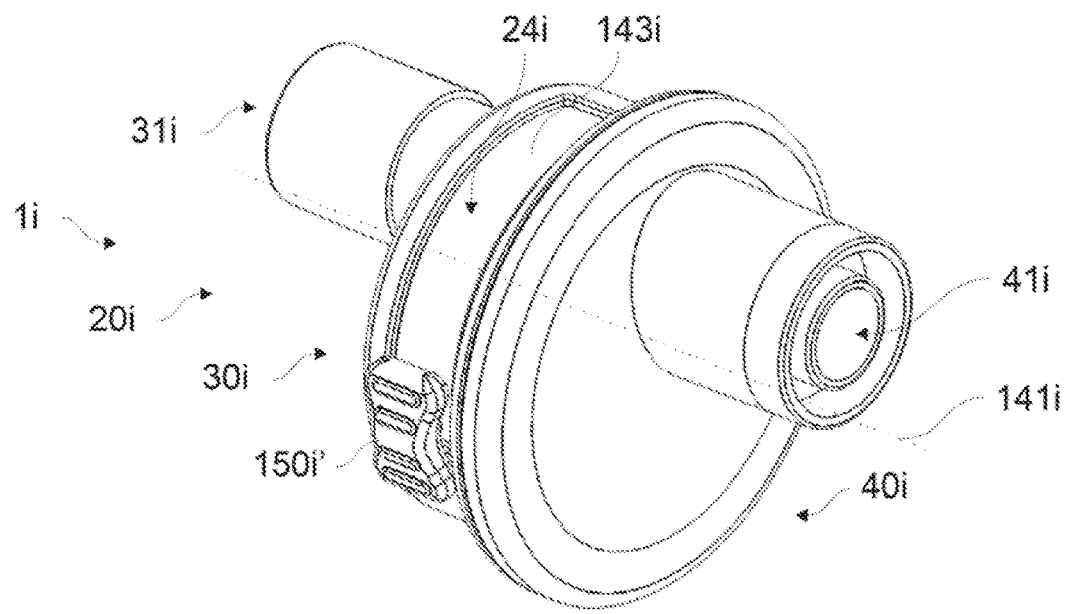
FIG. 32 is a perspective view of the HME device according to a ninth embodiment of the present invention.
Figure 33:
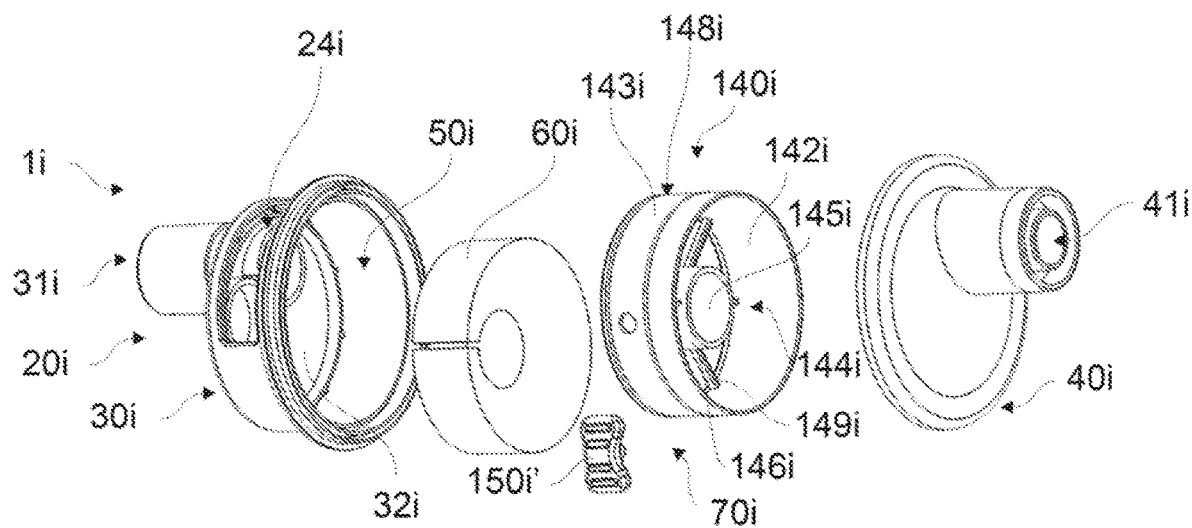
FIG. 33 is an exploded partial view of the HME device according to the ninth embodiment of the present invention.

FIGS. 32 and 33 show a ninth embodiment of the present invention. FIG. 32 shows an HME device 1*i*, in which the housing 20*i* has an inlet-side housing half 30*i* with the inlet opening 31*i* and an outlet-side housing half 40*i* with the outlet opening 41*i*. In addition, FIG. 32 shows an axis of rotation 141*i*, about which the HME storage space 140*i* is arranged rotatably. The housing 20*i* has, according to the embodiment shown in FIG. 32, a housing window 24*i*, through which an outer wall section 143*i* of the HME storage frame 140i is exposed to the outside. In addition, FIG. 32 shows an adjusting element 150i' in the form of a radially displaceable sliding switch, which element or switch is in functional connection with the HME storage frame 140i through the housing window 24i. The HME storage frame 140i is mounted rotatably by moving the adjusting element 150i' about the axis of rotation 141i.

FIG. 33 shows an exploded view of the HME device 1i according to the ninth embodiment of the present invention. FIG. 33 shows that the HME storage frame 140i has an outer ring section 148i and a storage frame passage channel 144i within the outer ring section 148i, the HME chamber 50i for the HME medium 60i being formed by an inner wall section 32i of the housing 20i, by an inner wall section 142i of the outer ring section 148i and by an outer wall section 146i of the storage frame passage channel 144i. The inner wall section 145i of the storage frame passage channel 142i corresponds to an inner wall section of the bypass channel in the bypass mode (not shown). FIG. 33 shows, in addition, that the storage frame passage channel 144i is held by connection struts 149i in the outer ring section 148i. The HME device 1i has, further, a switching mechanism 70i according to FIG. 33.

Figure 34:
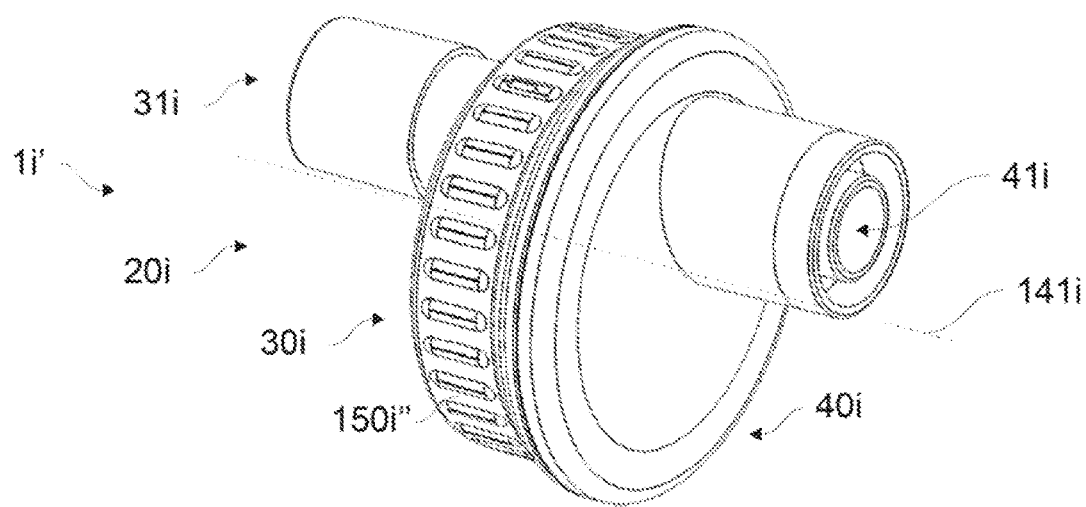
FIG. 34 is a perspective view of the HME device according to a tenth embodiment of the present invention.
Figure 35:
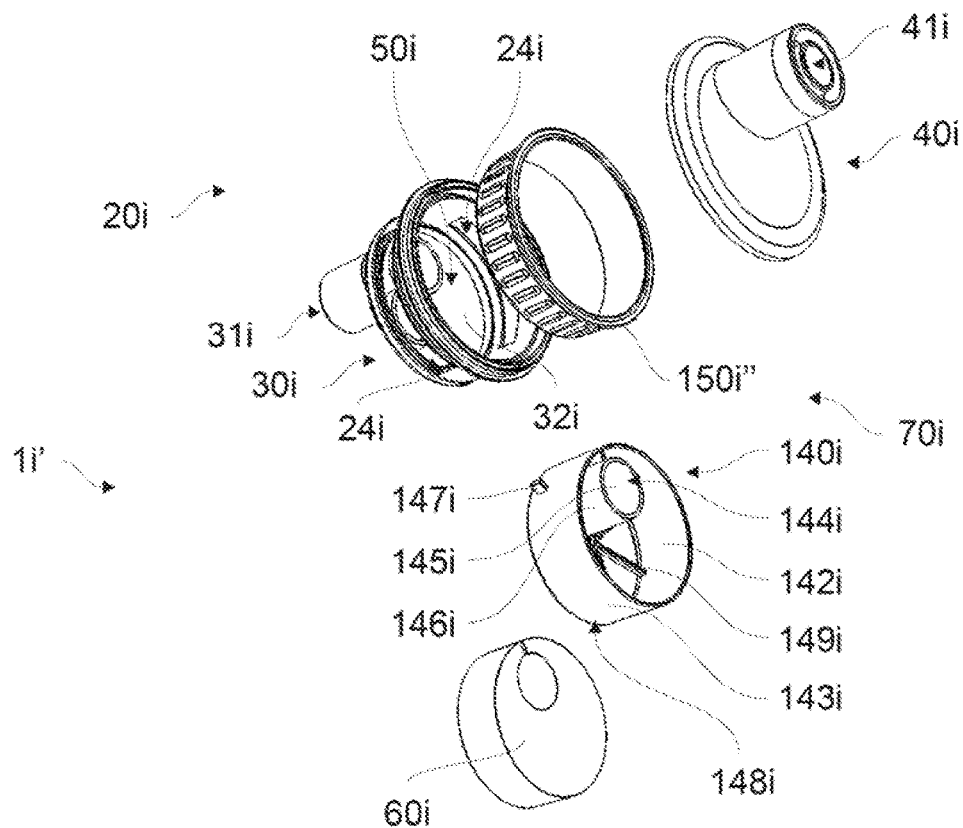
FIG. 35 is a perspective exploded view of the HME device according to the tenth embodiment of the present invention.

FIGS. 34 and 35 show an HME device 1i' according to a tenth embodiment of the present invention. Especially the adjusting element 150i''' of the tenth embodiment, which shows the essential distinctive feature compared to the ninth embodiment, will be described below. The adjusting element 150i''' is functionally connected here to the HME storage frame 140i via a projection 147i from the outer wall section 143i of the outer ring section 148i through the housing window 24i. As a result, a user can exert a corresponding rotary motion on the HME storage frame 140i by rotating the ring-shaped adjusting element 150i'''.

While specific embodiments of the invention have been shown and described in detail to illustrate the application of the principles of the invention, it will be understood that the invention may be embodied otherwise without departing from such principles.

APPENDIX: LIST OF REFERENCE CHARACTERS 1a, 1b, 1c, 1d, 1f, 1g, 1h, 1i, 1i' HME device
20a, 20b, 20c, 20d, 20e, 20f, 20g, 20h, 200i Housing
21a, 21d, 21h Axis of rotation
22f First inner wall section
23f Second inner wall section
24f, 24i Housing window
30a, 30b, 30c, 30d, 30e, 30f, 30g, 30h, 30i Inlet-side housing half
31a, 31b, 31c, 31d, 31e, 31f, 31g, 31h, 31i Inlet opening
32a, 32b, 32f, 32g, 32i Inner wall section
33a First inlet holes
34a Second inlet holes
35a Inlet diaphragms
36a Inlet diaphragm passages
37g Fluid inlet channel
38a Holding element
39a Outer wall section
40a, 40b, 40c, 40d, 40e, 40f, 430g, 40h, 40i Outlet-side housing half
41a, 41b, 41c, 41d, 41e, 41f, 41g, 41h, 41i Outlet opening
42a, 42b, 42c, 42f Inner wall section
43a Outlet holes
44a Outlet diaphragms
45a Turning handle
46g Fluid outlet channel
47a Outer wall section
50a, 50b, 50c, 50d, 50e, 50f, 50g, 50h, 50i HME chamber
60a, 60b, 60c, 60d, 60e, 60f, 60g, 60h, 60i HME medium
61g Stepped passage channel
70a, 70b, 70c, 70d, 70e, 70f, 70g, 70h, 70i Switching mechanism
80a, 80b, 80d, 80e, 80f, 80h Bypass channel
81b, 81d, 81e Inner wall section
82h Bypass chamber
90b, 90c, 90d, 90e Displacing device
91b, 91c, 91d, 91e Outer wall section
92b, 92c, 92d, 92e Outer wall section
93b, 93c Partition section
94b, 94c Partition section
95b, 95c, 95d Manual actuating device
96d, 96e Separating device
97d, 97e Separating device
98b, 98d Coupling element
99b, 99d Sealing element
100f Hollow section
101f Axis of rotation
102f Inner wall section
103f First outer wall section
104f Second outer wall section
110g First fluid switchover channel
120g Second fluid switchover channel
130h Fluid inlet channel
131h Inlet opening
132h Passage opening
133h Lateral opening section
134h Frontal opening section
135h Wall section
140i HME storage frame
141i Axis of rotation
142i Inner wall section
143i Outer wall section
144i Storage frame passage channel
145i Inner wall section
146i Outer wall section
147i Projection
148i Outer ring section
149i Connection struts
150i', 150i''' Adjusting element

What is claimed is:

1. A heat and moisture exchanger or humidification moisture exchanger (HME) device for use in a breathing circuit of a ventilation system, the device comprising:

a housing with an inlet opening and an outlet opening, wherein the housing comprises an inlet-side housing half and an outlet-side housing half, wherein a fluid inlet channel is arranged in the inlet-side housing half, wherein the fluid inlet channel and the inlet-side housing half are arranged rotatably in relation to one another, wherein the fluid inlet channel comprises a passage opening, wherein the fluid inlet channel comprises an inlet opening, wherein the inlet opening of the housing is also the inlet opening of the fluid inlet channel, wherein the housing comprises an HME chamber arranged between the inlet opening of the housing and the outlet opening for receiving an HME medium and a bypass channel, wherein the passage opening comprises a lateral opening section and a frontal opening section, wherein a flow direction of the lateral opening section is directed perpendicular to a flow direction of the inlet opening of the fluid inlet channel and of the frontal opening section, wherein said fluid inlet channel comprises a wall section which is arranged adjacent to said lateral opening section in said fluid inlet channel in parallel to the flow direction of said lateral opening section; and
a switching mechanism switching over between an HME mode providing an HME fluid passage from the inlet opening of the housing through the HME chamber to the outlet opening and a bypass mode providing a fluid bypass passage from the inlet opening past the HME chamber through the bypass channel to the outlet opening, wherein the bypass channel is blocked from the HME chamber in the bypass mode, wherein the passage opening is directed into the HME chamber when the switching mechanism is in the HME mode and is directed into the bypass channel when the switching mechanism is in the bypass mode.

2. A device in accordance with claim 1, wherein:
an edge of the wall section is arranged adjacent to the lateral opening section;
the lateral opening section is configured to receive a flow of fluid in the flow direction of the lateral opening section and the inlet opening and the frontal opening section are configured to receive a flow of fluid in the flow direction of the inlet opening and the frontal opening section.

3. A device in accordance with claim 2, wherein:
the bypass channel is arranged radially outward from the passage opening, the fluid inlet channel, and the inlet and outlet openings of the housing.

4. A device in accordance with claim 1, wherein:
the bypass channel is arranged radially outward from the fluid inlet channel.

5. A device in accordance with claim 1, wherein:
the bypass channel is arranged radially outward from the passage opening.

6. A device in accordance with claim 1, wherein:
the bypass channel is arranged radially outward from the inlet opening of the housing.

7. A device in accordance with claim 1, wherein:
the bypass channel is arranged radially outward from the inlet and outlet openings of the housing.

8. A heat and moisture exchanger or humidification moisture exchanger (HME) device comprising:
a housing with an inlet-side housing half defining a housing inlet opening, and with an outlet-side housing half defining a housing outlet opening;
a fluid inlet channel rotatably mounted in said inlet-side housing half, said fluid inlet channel defining a passage opening, said fluid inlet channel defining a channel inlet opening corresponding to said housing inlet opening, said housing defining an HME chamber arranged between said housing inlet opening and said housing outlet opening, said HME chamber being configured to receive an HME medium, said housing defining a bypass channel, said fluid inlet channel defining a lateral opening section and a frontal opening section, wherein a flow direction of said lateral opening section is perpendicular to a flow direction of said channel inlet opening and is perpendicular to a flow direction of said frontal opening section;
a wall section in said fluid inlet channel arranged parallel to said flow direction of said lateral opening section, said wall section being arranged adjacent to said lateral opening section; and
a switching mechanism switching between an HME mode providing an HME fluid passage from said housing inlet opening through the HME chamber to said housing outlet opening and a bypass mode providing a fluid bypass passage from said housing inlet opening past said HME chamber through said bypass channel to said housing outlet opening, wherein said bypass channel is blocked from said HME chamber in said bypass mode, said passage opening being directed into said HME chamber when said switching mechanism is in said HME mode, said passage opening being directed into said bypass channel when said switching mechanism is in said bypass mode.

9. A device in accordance with claim 8, wherein:
an edge of said wall section is arranged adjacent to said lateral opening section;
said lateral opening section defines a lateral opening section plane;
said channel inlet opening defines a channel inlet opening plane;
said frontal opening defines a frontal opening plane;
said lateral opening section plane is perpendicular to said channel inlet opening plane and perpendicular to said frontal opening section plane.

10. A device in accordance with claim 9, wherein:
said bypass channel is arranged radially outward from said passage opening, said fluid inlet channel, and said housing inlet and housing outlet openings.

11. A device in accordance with claim 8, wherein:
said bypass channel is arranged radially outward from said housing inlet opening.

12. A device in accordance with claim 8, wherein:
said bypass channel is arranged radially outward from said passage opening.

13. A device in accordance with claim 8, wherein:
said bypass channel is arranged radially outward from said fluid inlet channel.

14. A heat and moisture exchanger or humidification moisture exchanger (HME) device for use in a breathing circuit of a ventilation system, the device comprising:
a housing comprising an HME chamber, a fluid inlet channel, a housing inlet opening, a housing outlet opening, an inlet-side housing portion and an outlet-side housing portion, wherein at least a portion of the fluid inlet channel is arranged in an interior of the inlet-side housing portion, wherein the fluid inlet channel and the inlet-side housing half are arranged rotatably in relation to one another, the fluid inlet channel comprising a passage section comprising a passage opening, the passage opening comprising at least one lateral opening and at least one frontal opening, wherein the fluid inlet channel comprises a fluid inlet channel opening corresponding to the housing inlet opening, the HME chamber being arranged between the housing inlet opening and the housing outlet opening for receiving a HME medium and a bypass channel, the at least one lateral opening being configured to receive a flow of fluid in a first direction, the frontal opening being configured to receive a flow of fluid in a second direction, the first direction being perpendicular to the second direction, wherein the fluid inlet channel comprises a wall section arranged adjacent to the at least one lateral opening in the fluid inlet channel, the wall section being parallel to the first direction; and
a switching mechanism switching over between an HME mode providing an HME fluid passage from the housing inlet opening through the HME chamber to the housing outlet opening and a bypass mode providing a fluid bypass passage from the housing inlet opening past the HME chamber through the bypass channel to the housing outlet opening, the bypass channel not being in fluid communication with the HME chamber in the bypass mode, wherein a fluid passing through the passage opening is directed into the HME chamber when the switching mechanism is in the HME mode and the fluid passing through the passage opening is directed into the bypass channel when the switching mechanism is in the bypass mode.

15. A device in accordance with claim 14, wherein an edge of the wall section is arranged adjacent to the at least one lateral opening.

16. A device in accordance with claim 15, wherein the bypass channel is arranged radially outward from the passage opening, the fluid inlet channel, and the housing inlet opening and the housing outlet opening.

17. A device in accordance with claim 14, wherein the bypass channel is arranged radially outward from the fluid inlet channel.

18. A device in accordance with claim 14, wherein the bypass channel is arranged radially outward from the passage opening.

19. A device in accordance with claim 14, wherein the bypass channel is arranged radially outward from the housing inlet opening.

20. A device in accordance with claim 14, wherein the bypass channel is arranged radially outward from the housing inlet opening and the housing outlet opening.

* * * * *